US006867036B1

(12) United States Patent
Vile et al.

(10) Patent No.: US 6,867,036 B1
(45) Date of Patent: Mar. 15, 2005

(54) GENE EXPRESSION BY POSITIVE FEEDBACK ACTIVATION OF A CELL TYPE-SPECIFIC PROMOTER

(75) Inventors: Richard G. Vile, Rochester, MN (US); Michael Gough, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 269 days.

(21) Appl. No.: 09/721,391

(22) Filed: Nov. 22, 2000

Related U.S. Application Data

(60) Provisional application No. 60/167,085, filed on Nov. 23, 1999.

(51) Int. Cl.[7] .................. C12N 15/00; C12N 15/63; C07H 21/04
(52) U.S. Cl. ............... 435/320.1; 435/455; 536/24.1
(58) Field of Search .............................. 424/93.1, 93.2; 435/320.1, 70.1; 514/44; 536/23.1–23.5, 24.1

(56) References Cited

U.S. PATENT DOCUMENTS

| | | | |
|---|---|---|---|
| 5,137,805 A | | 8/1992 | Kingston et al. |
| 5,738,985 A | | 4/1998 | Miles et al. |
| 5,739,018 A | * | 4/1998 | Miyanohara et al. ..... 435/172.3 |
| 5,756,343 A | * | 5/1998 | Wu et al. ................ 435/252.3 |
| 5,770,581 A | | 6/1998 | Weichselbaum et al. |
| 5,827,685 A | | 10/1998 | Lindquist |
| 6,034,228 A | | 3/2000 | Norris et al. |
| 6,037,329 A | * | 3/2000 | Baird et al. .................... 514/44 |
| 2002/0042127 A1 | * | 4/2002 | Russel et al. ................ 435/346 |

OTHER PUBLICATIONS

He et al., Glycogen Synthase Kinase 3B and Extracellular Signal–Regulated Kinase Inactivate Heat Shock Transcription Factor 1 by Facilitating the Disappearance of Transcriptionally Active Granules after Heat Shock; Mol. and Cell Bio, Nov. 1998, p 6624–6633.*

Cao et al., A Safe, Effective in Vivo Gene Therapy for Melanoma Using Tyrosinase Promoter–Driven Cytosine Deaminase Gene, In vivo 13: 181–188 (1999).*

Takeda et al., Functional Analysis of the cDNA Encoding Human Tyrosinase Precursor; Biochemical and Biophysical Research Communications; vol. 162, No. 3 1989, Aug. 15, 1989, pp. 984–990.*

Eck et al., Gene–Based Therapy Chapter V, Goodman & Gilman's The Pharmacological Basis of Therapeutics; pp. 77–101.*

Gura; Systems for Identifying New Drugs Are Often Faulty; www.sciencemag.org; Science; vol. 278, Nov. 7, 1997, p 1041–1042.*

Rozenberg et al., Alternative gene delivery; S.T.P Pharma Sciences 11 (1) 21–30 2001.*

Nishikawa et al., Nonviral Vectors in the New Millennium: Delivery Barriers in Gene Transfer; Human Gene Therapy 12:861–870 (May 20, 2001).*

Balicki et al., Gene Therapy of Human Disease; Medicine 81:69–86, 2002.*

Emiliusen et al. A transcriptional feedback loop for tissue–specific expression of highly cytotoxic genes which incorporates an immunostimulatory component. Gene therapy 8:987–998, 2001.*

Nettelbeck et al. Gene therapy designer promoters for tumour targeting. TIG 16:174–181, 2000.*

Dang et al. Gene therapy and translational cancer research. Clin. Cancer Res. 5:471–474, 1999.*

Verma et al. Gene therapy—promises, problems and prospects. Nature 389:239–242, 1997.*

Sato et al. Enhanced and specific gene expression via tissue–specific production of Cre recombinaase using adenovirus vector. Biochem. Biophys. Res. Commun. 244:455–462, 1998.*

Cao et al., "A safe, effective in vivo gene therapy for melanoma using tyrosinase promoter–driven cytosine deaminase gene," In Vivo (Greece), 1999, 13(2):181–187, Abstract only.

Mivechi et al., "Stable Overexpression of Human HSF–1 in Murine Cells Suggests Activation Rather Than Expression of HSF–1 to be the Key Regulatory Step in the Heat Shock Gene Expression," J. Cell. Biochem., 1995, 59:266–280.

Miyazaki et al., "Activation of of Human Multidrug Resistance–1 Gene Promoter in Response to Heat Shock Stress," Biochem. Biophys. Res. Comm., 1992, 187(2):677–684.

Park et al., "Augmentation of Melanoma–Specific Gene Expression Using a Tandem Melanocyte–Specific Enhancer Results in Increased Cytotoxicity of the Purine Nucleoside Phosphorylase Gene in Melanoma," Human Gene Therapy, 1999, 10:889–898.

(List continued on next page.)

Primary Examiner—David Guzo
Assistant Examiner—Quang Nguyen
(74) Attorney, Agent, or Firm—Fish & Richardson P.C., P.A.

(57) ABSTRACT

A nucleic acid construct is described which provides cell type-specific expression of a therapeutic transgene. The construct utilizes a cell type-specific promoter which drives expression of the transgene. A positive feedback loop is introduced through the addition of a amplification promoter element operably linked to the therapeutic transgene and by providing, either as part of the same construct, or in a different construct, a transcription activator for activating the amplification promoter element. In one embodiment, the amplification promoter element is a heat shock response element (HSE) and the transcription activator is HSF-1. The construct enables functional targeting of a therapeutic gene while avoiding undesirable effects in non-targeted cells, by combining sufficiently high-level expression to promote a desirable therapeutic outcome with exceptional tissue specificity. A series of promoter elements, constructs, vectors, and therapeutic approaches is presented for gene therapy of tumors such as melanoma and other genetic diseases.

13 Claims, 18 Drawing Sheets

OTHER PUBLICATIONS

Provisional Appl. No. 60/193,977, Filed Mar. 31, 2000.
GenBank Accession No. A23284.
GenBank Accession No. D49357.
GenBank Accession No. D86181.
GenBank Accession No. L12392.
GenBank Accession No. M11147.
GenBank Accession No. M13142.
GenBank Accession No. M14338.
GenBank Accession No. M60091.
GenBank Accession No. M26927.
GenBank Accession No. M68840.
GenBank Accession No. S64699.
GenBank Accession No. S56903.
GenBank Accession No. U39817.
GenBank Accession No. U49897.
GenBank Accession No. V00497.
GenBank Accession No. V00571.
GenBank Accession No. X01712.
GenBank Accession No. X02747.
GenBank Accession No. X03633.
GenBank Accession No. X13255.
GenBank Accession No. X15149.
GenBank Accession No. X55079.
GenBank Accession No. X55330.
GenBank Accession No. X59798.
GenBank Accession No. Z25884.
GenBank Accession No. Z48804.
GenBank Accession No. AF057310.
Alexandropoulos et al., "v–Fps–responsiveness in the Egr–1 promoter is mediated by serum response elements," *Nucleic Acids Res.*, 1992, 20(9):2355–2359.
Attar and Gilman, "Expression Cloning of a Novel Zinc Finger Protein That Binds to the c–fos Serum Response Element," *Mol. Cell. Biol.*, 1992, 12(5):2432–2443.
Bae et al., "Genomic Differences between the Diabetogenic and Nondiabetogenic Variants of Encephalomyocarditis Virus," *Virology*, 1989, 170:282–287.
Baler et al., "Activation of Human Heat Shock Genes Is Accompanied by Oligomerization, Modification, and Rapid Translocation of Heat Shock Transcription Factor HSF1," *Mol. Cell. Biol.*, 1993, 13(4):2486–2496.
Bateman et al., "Fusogenic Membrane Glycoproteins As a Novel Class of Genes for the Local and Immune–mediated Control of Tumor Growth," *Cancer Res.*, 2000, 60:1492–1497.
Bentley et al., "Melanocyte–Specific Expression of the Human Tyrosinase Promoter: Activation by the Microphthalmia Gene Product and Role of the Initiator," *Mol. Cell. Biol.*, 1994, 14(12):7996–8006.
Berger et al., "Natural and Synthetic Heat Shock Protein Gene Promoters Assayed in *Drosophila* Cells," *Somatic Cell and Molecular Genetics*, 1986, 12(5):433–440.
Blackburn et al., "Adenoviral–mediated Transfer of a Heat–inducible Double Suicide Gene into Prostate Carcinoma Cells," *Cancer Res.*, 1998, 58:1358–1362.
Broach et al., "Vectors for High–Level, Inducible Expression of Cloned Genes in Yeast," *Experimental Manipulation of Gene Expression*, Inouye (ed.), 1983, Academic Press, Inc., Orlando, Florida, Chapter 5, pp. 83–117.
Carrol and Taichman, "Characterization of the human involucrin promoter using a transient β–galactosidase assay," *J. Cell Science*, 1992, 103(4):925–930.

Chaubal et al., "Ep–CAM—A Marker for the Detection of Disseminated Tumor Cells in Patients Suffering from SCCHN," *Anticancer Research*, 1999, 19(3B):2237–2242.
Cohen et al., "Complete nucleotide sequence of an attenuated hepatitis A virus: Comparison with wild–type virus," *Proc. Natl. Acad. Sci. USA*, 1987, 84:2497–2501.
Craig, "The Heat Shock Response," *Crit. Rev. Biochem.*, 1985, 18(3):239–280.
Datta et al., "Ionizing radiation activates transcription of the EGRI gene via CArG elements," *Proc. Natl. Acad. Sci. USA*, 1992, 89:10149–10153.
Datta et al., "Reactive oxygen intermediates target CC(A/T)$_6$GG sequences to mediate activation of the early growth response 1 transcription factor gene by ionizing radiation," *Proc. Natl. Acad. Sci. USA*, 1993, 90:2419–2422.
Duechler et al., "Evolutionary relationships within the human rhinovirus genus: Comparison of serotypes 89, 2, and 14," *Proc. Natl. Acad. Sci. USA*, 1987, 84:2605–2609.
Diaz et al., "Exchange of Viral Promoter/Enhancer Elements with Heterologous Regulatory Sequences Generates Targeted Hybrid Long Terminal Repeat Vectors for Gene Therapy of Melanoma," *J. Virol.*, 1998, 72:789–795.
Diaz et al., "A lentiviral vector expressing a fusogenic glycoprotein for cancer gene therapy," *Gene Ther.*, 2000, 7:1656–1663.
Drabent et al., "In vitro transcription of a human hsp 70 heat shock gene by extracts prepared from heat–shocked and non–heat–shocked human cells," *Nucl. Acids Res.*, 1986, 14(22):8933–8948.
Earle et al., "The Complete Nucleotide Sequence of a Bovine Enterovirus," *J. Gen. Virol.*, 1988, 69:253–263.
Fielding et al., "A Hyperfusogenic Gibbon Ape Leukemia Envelope Glycoprotein: Targeting of a Cytotoxic Gene by Ligand Display," *Human Gene Ther.*, 2000, 11:817–826.
Ghebranious et al., "Developmental Control of Transcription of the Cat Reporter Gene by a Truncated Mouse Alphafetoprotein Gene Regulatory Region in Transgenic Mice," *Mol. Reprod. Dev.*, 1995, 42:1–6.
Goldenberg et al., "Purified Human Factor Activates Heat Shock Promoterin a HeLa Cell–free Transcription System," *J. Biol. Chem.*, 1988, 263(36):19734–19739.
Helftenbein et al., "Expression of the Uteroglobin Promoter in Epithelial Cells Lines from Endometrium," *Ann. N.Y. Acad. Sci.*, 1991, 622:69–79.
Hogen et al. (eds.), *Manipulating the Mouse Embryo*, A Laboratory Manual, Second Edition, 1994, Cold Spring Harbor Laboratory Press, Plainview, N.Y. (Table of Contents only).
Holbrook et al., "Signaling events controlling the molecular response to genotoxic stress," *Stress–Inducible Cellular Responses*, Feige et al. (eds.), 1996, Birkhauser Verlage Basel/Switzerland, pp. 273–288.
Hughes et al., "The Complete Nucleotide Sequence of Coxsackievirus A21," *J. Gen. Virol.*, 1989, 70:2943–2952.
Iizuka et al., "Complete Nucleotide Sequence of the Genome of Coxsackievirus B1," *Virology*, 1987, 156:64–73.
Inchauspe et al., "Genomic structure of the human prototype strain H of hepatitis C virus: Comparison with American and Japanese isolates," *Proc. Natl. Acad. Sci. USA*, 1991, 88:10292–10296.
Jackson, "Initiation without an end," *Nature*, 1991,353(6339):14–15.

Jenkins et al., "The Complete Nucleotide Sequence of Coxsackievirus B4 and Its Comparison to Other Members of the Picornaviridae," *J. Gen. Virol.,* 1987, 68:1835–1848.

Kato et al., "Molecular cloning of the human hepatitis C virus genome from Japanese patients with non–A, non–B hepatitis," *Proc. Natl. Acad. Sci. USA,* 1990, 87:9524–9528.

Kirkin et al., "The Immunogenic Properties of Melanoma–Associated Antigens Recognized by Cytotoxic T Lymphocytes," *Exp. Clin. Immunogenet.,* 1998, 15:19–32.

Lai et al., "Evaluation of Cytokeratin 19 Fragment (CYFRA 21–1) as a Tumor Marker in Malignant Pleural Effusion," *Jpn J. Clin. Oncol.,* 1999, 29(9):421–424.

Lindquist, "The Heat–Shock Response," *Ann. Rev. Biochem.* 1986, 55:1151–1191.

Macejak and Sarnow, "Internal initiation of translation mediated by the 5' leader of a cellular mRNA," *Nature,* 1991, 353(6339):90–94.

Maga et al., "Expression of human lysozyme mRNA in the mammary gland of transgenic mice," *Trans. Res.,* 1994, 3:36–42.

Martin et al., "Retroviral Vector Targeting to Melanoma Cells by Single–Chain Antibody Incorporation in Envelope," *Human Gene Ther.,* 1998, 9:737–746.

McGrane et al., "Developmental regulation and tissue–specific expression of a chimaeric phosphoenolpyruvate carboxykinase/bovine growth hormone gene in transgenic animals," *J. Reprod. Fert. Suppl.,* 1990, 41:17–23.

Melcher et al., "Tumor immunogenicity is determined by the mechanism of cell death via induction of heat shock protein expression," *Nat. Med.,* 1998, 4(5):581–587.

Melcher et al., "Heat Shock Protein Expression in Target Cells Infected with Low Levels of Replication–Competent Virus Contributes to the Immunogenicity of Adenoviral Vectors," *Human Gene Ther.,*1999, 10:1431–1442.

Mirault et al., "Regulation of heat–shock genes: a DNA sequence upstream of *Drosophila hsp 70* genes is essential for their induction in monkey cells," *EMBO J.,* 1982, 1(10):1279–1285.

Morgenstern and Land, "Advanced mammalian gene transfer: high titre retroviral vectors with multiple drug selection markers and a complementary helper–free packaging cell line," *Nucl. Acids Res.,* 1990, 18(12):3587–3596.

Naldini et al., "In Vivo Gene Delivery and Stable Transduction of Nondividing Cells by a Lentiviral Vector," *Science,* 1996, 272:263–267.

Neri et al., "Recombinant Anti–Human Melanoma Antibodies Are Versatile Molecules," *J. Invest. Dermatol.,* 1996, 107:164–170.

Nover (ed.), *Heat Shock Response of Eukaryotic Cells,* 1984, Springer–Verlag, Berlin (Table of Contents only).

Ohara et al., "Molecular Cloning and Sequence Determination of DA Strain of Theiler's Murine Encephalomyelitis Viruses," *Virology,* 1988, 164:245–255.

Osterling, "Prostate Specific Antigen: A Critical Assessment of the Most Useful Tumor Marker for Adenocarcinoma of the Prostate," *J. Urology,* 1991, 145:907–923.

Palmenberg et al., "The nucleotide and deducted amino acid sequences of the encephalomyocarditis viral polyprotein coding region," *Nucl. Acids Res.,* 1984, 12(6):2969–2985.

Pandha et al., "Genetic Prodrug Activation Therapy for Breast Cancer: A Phase I Clinical Trial of erbB–2–Directed Suicide Gene Expression," *J. Clin. Oncol.,* 1999, 17(7):2180–2189.

Paul et al., "The entire nucleotide sequence of the genome of human hepatitis A virus (isolate MBB)," *Virus Res.,* 1987, 8:153–171.

Pelham and Bienz, "A synthetic heat–shock promoter element confers heat–inducibility on the herpes simplex virus thymidine kinase gene," *EMBO J.,* 1982, 1(11):1473–1477.

Pelham, "Activation of heat–shock genes in eukaryotes," *Trends Genet.,* 1985, 1:31–35.

Peng and Russell, "Viral vector targeting," *Curr. Opin. Biotech.,* 1999,10:454–457.

Pinkus et al., "Are Keratin Proteins a Better Tumor Marker than Epithelial Membrane Antigen?" *Am. J. Clin. Pathol.,* 1986, 85:269–277.

Platenburg et al., "Expression of human lactoferrin in milk of transgenic mice," *Trans. Res.,* 1994, 3:99–108.

Qureshi et al., "v–Src Activates Mitogen–responsive Transcription Factor Egr–1 via Serum Response Elements," *J. Biol. Chem.,* 1991, 266(17):10802–10806.

Racaniello and Baltimore, "Molecular cloning of poliovirus cDNA and determination of complete nucleotide sequence of the viral genome," *Proc. Natl. Acad. Sci. USA,* 1981, 78(8):4887–4891.

Ritossa, "A New Puffing Pattern Induced by Temperature Shock and DNP in Drosophila," *Experientia,* 1962, 18:571–573.

Ryan et al., "The complete nucleotide sequence of enterovirus type 70: relationships with other members of the Picornaviridae," *J. Gen. Virol.,* 1990, 71:2291–2299.

Sambrook et al. (eds.), *Molecular Cloning—A Laboratory Manual,* Second Edition, 1989, Cold Spring Harbor Laboratory Press, Chapters 16 and 17, pp. 16.1–17.44.

Schrewe et al., "Cloning of the Complete Gene for Carcinoembryonic Antigen: Analysis of Its Promoter Indicates a Region Conveying Cell Type–Specific Expression," *Mol. Cell. Biol.,* 1990, 10(6):2738–2748.

Shinoura et al., "Adenovirus–mediated Transfer of p33$^{ING1}$ with p53 Drastically Augments Apoptosis in Gliomas," *Cancer Res.,* 1999, 59:5521–5528.

Skern et al., "Human rhinovirus 2: complete nucleotide sequence and proteolytic processing signals in the capsid protein region," *Nucl. Acids Res.,* 1985, 13(6):2111–2126.

Sonenberg and Meerovitch, "Translation of Poliovirus mRNA," *Enzyme,* 1990, 44:278–291.

Sorger, "Heat Shock Factor and the Heat Shock Response, "*Cell,* 1991, 65:363–366.

Srivastava et al., "Heat Shock Proteins Come of Age: Primitive Functions Acquire New Roles in an Adaptive World," *Immunity,* 1998, 8:657–665.

Stanway et al., "Comparison of the complete nucleotide sequences of the genomes of the neutovirulent poliovirus P3/Leon/37 and its attenuated Sabin vaccine derivative P3/Leon 12$a_1$b," *Proc. Natl. Acad. Sci. USA,* 1984, 81:1539–1543.

Todryk et al., "Heat Shock Protein 70 Induced During Tumor Cell Killing Induces Thl Cytokines and Targets Immature Dendritic Cell Precursors to Enhance Antigen Uptake," *J. Immunol.,* 1999, 163:1398–1408.

Vile et al., "Tissue–Specific Gene Expression from Mo–MLV Retroviral Vectors with Hybrid LTRs Containing the Murine Tyrosinase Enhancer/Promoter," *Virology,* 1995, 214:307–313.

Vile et al., "Strategies for achieving multiple layers of selectivity in gene therapy," *Mol. Med. Today,* 1998, 4:84–92.

Voellmy et al., "Isolation and functional analysis of a human 70,000–dalton heat shock protein gene segment," *Proc. Natl. Acad. Sci. USA,* 1985, 82:4949–4953.

Wong et al., "Human GM–CSF: Molecular Cloning of the Complementary DNA and Purification of the Natural and Recombinant Proteins," *Science,* 1985, 228:810–815.

Wu et al., "Structure and Expression of the Human Gene Encoding Major Heat Shock Protein HSP70," *Mol. Cell. Biol.,* 1985, 5(2):330–341.

Wu et al., "Human HSP70 promoter contains at least two distinct regulatory domains," *Proc. Natl. Acad. Sci. USA,* 1986, 83:629–633.

Zufferey et al., "Multiply attenuated lentiviral vector achieves efficient gene delivery in vivo," *Nat. Biotechnol.,* 1997, 15:871–875.

Zuo et al., "Multiple Layers of Regulation of Human Heat Shock Transcription Factor 1," *Mol. Cell. Biol.,* 1995, 15(8):4319–4330.

* cited by examiner

AGAATGTTCTAGAAG   (ACTGGAGAT)       TYR 300bp --

HSE     ......    ......(TURN)$_n$... ......E-Box

Tel.CeB6

CMV-GALV
CMV-βGal
HSE-Tyr-GALV
Tyr-GALV

Tel.CeB6

HSE-Tyr-GALV + Heat
Tyr-GALV + Heat
HSE-Tyr-GALV + mHSF-1
Tyr-GALV + mHSF-1

Mel 624

CMV-GALV
CMV-βGal
HSE-Tyr-GALV
Tyr-GALV

Mel 624

HSE-Tyr-GALV + Heat
Tyr-GALV + Heat
HSE-Tyr-GALV + 5µg mHSF-1
Tyr-GALV + 5µg mHSF-1

Mel 624: 5μg HSE-Tyr-GALV + CMV-βGal

0μg  1μg  2μg  5μg  10μg

Mel 624: 5μg HSE-Tyr-GALV + mHSF-1

0μg  1μg  2μg  5μg  10μg

Mel 624

Syncytia Formation with Time Following Infection (hrs)

| Vector | t=0 | t=24 | t=48 | t=72 | t=96 | t=120 |
|---|---|---|---|---|---|---|
| pBabe Puro | - | - | - | - | - | - |
| pBabe GALV | - | + | ++ | +++ | ++++ | +++ |
| pBabe GALV-HSF-1-(wtLTR) | - | + | + | +++ | ++++ | ++++ |
| pBabe GALV-HSF-1-(HSE Tyr LTR) | - | - | - | + | +++ | ++++ |

Tel

| Vector | t=0 | t=24 | t=48 | t=72 | t=96 | t=120 |
|---|---|---|---|---|---|---|
| pBabe Puro | - | - | - | - | - | - |
| pBabe GALV | - | + | ++ | ++++ | ++++ | ++ |
| pBabe GALV-HSF-1-(wtLTR) | - | + | +++ | ++++ | ++++ | ++ |
| pBabe GALV-HSF-1-(HSE Tyr LTR) | - | - | - | - | - | - |

FIG. 14B

SEQUENCE LISTING

<160> NUMBER OF SEQ ID NOS: 7

<210> SEQ ID NO 1
<211> LENGTH: 300
<212> TYPE: DNA
<213> ORGANISM: Homo sapiens

<400> SEQUENCE: 1

| tcatttgcaa | ggtcaaatca | tcattagttt | tgtagtctat | taactgggtt | tgcttaggtc | 60 |
| aggcattatt | attactaacc | ttattgttaa | tattctaacc | ataagaatta | aactattaat | 120 |
| ggtgaataga | gtttttcact | ttaacatagg | cctatcccac | tggtgggata | cgagccaatt | 180 |
| cgaaagaaaa | gtcagtcatg | tgcttttcag | aggatgaaag | cttaagataa | agactaaaag | 240 |
| tgtttgatgc | tggaggtggg | agtggtatta | tataggtctc | agccaagaca | tgtgataatc | 300 |

<210> SEQ ID NO 2
<211> LENGTH: 15
<212> TYPE: DNA
<213> ORGANISM: Artificial Sequence
<220> FEATURE:
<223> OTHER INFORMATION: oligonucleotide for PCR

<400> SEQUENCE: 2
agaatgttct agaag                                                          15

```
<210> SEQ ID NO 3
<211> LENGTH: 21
<212> TYPE: DNA
<213> ORGANISM: Artificial Sequence
<220> FEATURE:
<223> OTHER INFORMATION: oligonucleotide for PCR

<400> SEQUENCE: 3
atggagaaaa aaatcactgg a                                          21

<210> SEQ ID NO 4
<211> LENGTH: 21
<212> TYPE: DNA
<213> ORGANISM: Artificial Sequence
<220> FEATURE:
<223> OTHER INFORMATION: oligonucleotide for PCR

<400> SEQUENCE: 4
gagacgaaaa acatattctc a                                          21

<210> SEQ ID NO 5
<211> LENGTH: 10
<212> TYPE: DNA
<213> ORGANISM: Artificial Sequence
<220> FEATURE:
<223> OTHER INFORMATION: promoter element
<220> FEATURE:
<221> NAME/KEY: misc_feature
<222> LOCATION: (1)...(10)
<223> OTHER INFORMATION: n = A,T,C or G

<400> SEQUENCE: 5 ngaannttcn                                                       10

<210> SEQ ID NO 6
<211> LENGTH: 10
<212> TYPE: DNA
<213> ORGANISM: Artificial Sequence
<220> FEATURE:
<223> OTHER INFORMATION: promoter element
<220> FEATURE:
<221> NAME/KEY: misc_feature
<222> LOCATION: (1)...(10)
<223> OTHER INFORMATION: n = A,T,C or G

<400> SEQUENCE: 6 nttcnngaan                                                       10

<210> SEQ ID NO 7
<211> LENGTH: 9
<212> TYPE: DNA
<213> ORGANISM: Artificial Sequence
<220> FEATURE:
<223> OTHER INFORMATION: linker

<400> SEQUENCE: 7 actggagat                                                         9
```

GENE EXPRESSION BY POSITIVE FEEDBACK ACTIVATION OF A CELL TYPE-SPECIFIC PROMOTER

RELATED APPLICATIONS

This application claims priority under 35 U.S.C. § 119(e) to U.S. Provisional Application Ser. No. 60/167,085, filed Nov. 23, 1999, the entirety of which is incorporated by reference herein.

FIELD OF THE INVENTION

The invention is related to the area of gene therapy. In particular, the invention is related to vectors comprising cell type-specific promoter elements that selectively express cytotoxic genes in tumor cells.

BACKGROUND OF THE INVENTION

A major unresolved problem in the field of gene therapy is how to achieve the expression of a therapeutic gene in target cells where its effects are desired while avoiding its expression in non-target cells. The problem is especially acute when the transgene has the capacity to harm non-tumor cells and tissues, for example, where a suicide gene is used to destroy a tumor. Two basic approaches have been attempted: the transgene can be delivered in the form of a vector targeted specifically to certain types of cells (vector targeting; see, e.g., Peng and Russell, Cur. Opin. Biotech. 10: 454–457 (1999)) or the transgene can be cloned downstream of a cell type-specific promoter (transcriptional targeting; see Vile, et al, Mol. Med. Today 4: 84–92 (1998)). Targeting of vectors can also rely on physically administering them to a particular anatomical location, either by relying on the natural tropisms of the vectors or by engineering them to recognize a molecular target. A combination of these approaches offers the best hope for the systemic delivery of vectors to treat human disease. Vile, et al., supra.

A variety of cell type-specific promoters are known. Examples include promoters for tyrosinase (specific for melanoma cells and melanoctyes; see, Bentley, et al, Mol. Cell. Biol. 14; 7996–8006 (1994)), carcinoembryonic antigen (CEA, specific for colorectal cancer cells; see, e.g., Schrewe, et al., Mol. Cell. Biol. 10: 2738–2748 (1990)), alpha fetoprotein (specific for hepatocytes; see, e.g., Ghebranious, et al., Mol. Reprod. Dev. 42: 1–6 (1995)), erb-B2 (specific for breast cancer cells; see, e.g., Pandha, et al., J. Clin. Oncol. 17: 2180 (1999)) and myelin basic protein (specific for glioma cells; see, e.g., Shinoura, et al., Cancer Res. 59: 5521–5528 (1999)).

However, the use of cell type-specific promoters to induce the expression of cytotoxic agents in tumor cells is particularly problematic. The higher the potency of the suicide gene applied (e.g., toxicity), the greater the potential damage to non-tumor cells that receive the gene if the promoter controlling the suicide gene is not perfectly tumor-specific. Further, inadequate promoter specificity can have serious deleterious effects in non-target cells and tissues which are only revealed under certain conditions. For example, previous work has demonstrated that three tandem repeats of an enhancer element from the human tyrosinase gene (the tyrosinase distal element, TDE), when combined with a basal SV40 promoter, is sufficient to support highly selective expression of the cytokine GM-CSF in human melanoma cells (Diaz et al. J. Virol. 72: 789–95 (1998)). However, when the TDE-5V40 promoter is used to drive the expression of the envelope glycoprotein from Gibbon Ape Leukemia Virus (GALV), a highly cytotoxic fusogenic membrane glycoprotein (FMG), 3 of 9 non-melanoma cell lines showed significant amounts of cell killing (syncytium formation) after 72–96 hours, indicating that for this construct the TDE-5V40 promoter was not completely cell type-specific. Therefore, the high toxicity of proteins like GALV envelope glycoprotein, which makes them desirable as potent antitumor agents, will result in an unacceptable amount of bystander killing (killing of nearby normal cells) unless the expression of such agents can be made highly specific for their target cells.

While these problems can be overcome by developing promoters with higher specificity, high tissue specificity tends to be achieved at the expense of promoter strength, thereby undercutting the potency of the therapeutic gene.

SUMMARY OF THE INVENTION

It is an object of the invention to provide methods and materials to selectively express transgenes in a target tissue. It is also an object of the invention to provide methods and materials to amplify the activity of a cell type-specific promoter. It is another object of the invention to provide methods and materials using a cell type-specific promoter that controls expression of a cytotoxic gene, thereby enhancing the selective killing of targeted cells.

The invention further provides a new class of genes with both direct cytotoxic and immunostimulatory properties. It is still another object of the invention to provide materials such as cell type-specific promoters and constructs containing them. A further object of the invention is to pirovide targeted expression vectors comprising cell type-specific promoters. These and other objects of the invention are provided by one or more of the embodiments described below.

One embodiment of the invention provides a nucleic acid molecule comprising an amplification promoter element (e.g., a heat shock element), a cell type-specific promoter, and a cytotoxic gene under control of the cell type-specific promoter. The-nucleic acid molecule can optionally comprise a sequence encoding a amplification promoter transcription activator (e.g., HSF-1 or a constitutively active mutant thereof), that activates the amplification promoter element. For some embodiments, when the nucleic acid molecule is expressed in a target tissue, the level of mRNA expression from the construct is at least 100-fold higher or at least 1000-fold higher than if the construct is expressed in a non-target tissue.

Another embodiment of the invention provides a human tyrosinase promoter and a cytotoxic gene under control of the promoter. In one embodiment, the promoter is Tyr300.

A further embodiment of the invention provides a nucleic acid construct for positive feedback amplification of the expression of a transgene. The construct comprises a heat shock element, a promoter that controls expression of the transgene, and a sequence encoding a transcriptional activator. The transcriptional activator activates the heat shock element to increase the activity of the promoter, resulting in greater expression of the transgene and the sequence encoding the transcriptional activator. In one embodiment, the transcriptional activator can be HSF-1 or a constitutively active mutant of HSF-1. In another embodiment, the promoter is a cell type-specific promoter.

Still another embodiment provides a vector comprising a heat shock element, a cell type-specific promoter, and a cytotoxic gene under control of the cell type-specific promoter.

A further embodiment provides a pair of vectors. The first vector comprises a heat shock element, a cell type-specific promoter, and a cytotoxic gene under control of the cell type-specific promoter. The second vector comprises a sequence encoding a transcriptional activator that activates the heat shock element (e.g., such as HSF-1).

Yet another embodiment provides a method of treating a patient in need of tissue-selective gene therapy. In this embodiment, a vector comprising a heat shock element, a cell type-specific promoter, and a cytotoxic gene under control of the cell type-specific promoter is administered to the patient.

Another embodiment provides a method of treating a patient in need of targeted cytotoxic gene therapy. An effective amount of a vector is administered to the patient. The vector comprises a nucleic acid molecule comprising an enhancer, a target cell type-specific promoter, a cytotoxic gene under control of the target cell type-specific promoter, and a gene encoding a transcription factor that activates the enhancer.

Still another embodiment provides a method of specifically inducing expression of a transgene in a melanoma cell. The melanoma cell is transfected with a vector comprising a Tyr300 promoter and a transgene. The production of transgene mRNA is at least 100-fold higher in the melanoma cell than in non-melanoma cells.

The invention thus provides new tools and methods for the highly selective expression of transgenes in a desired target tissue.

BRIEF DESCRIPTION OF THE DRAWINGS

The objects and features of the invention can be better understood with reference to the following detailed description and accompanying drawings.

FIG. 3A indicates that the Tyr 115 base pair promoter is not comp ely inactive in non-melanoma cells. RT-PCR to determine expression of the CAT gene under the control of the Tyr115 base pair promoter was performed using RNA from a range of non-melanoma lines (lanes 2 and 3, HT1080; lanes 4 and 5, 293; lanes 12 and 13, A378M). Reverse transcriptase was omitted in the odd numbered lanes. Expression is observed in at least 2 non-melanoma cell lines (293, lane 4 and Tel CeB6, lane 6).

FIG. 4 demonstrates that HSE confers heat-shock and mHSF-1 inducibility on the melanoma-specific Tyr 300 base pair promoter. MeWo cells transfected with the Tyr 300-GM-CSF (condition 2) or the HSE-Tyr 300-FULL-GM-CSF plasmids (condition 6) express only very low amounts of GM-CSF, demonstrating that Tyr 300 is a very weak promoter. However, transfection of the human melanoma MeWo line with the TDE-5V40-GM-CSF plasmid (condition 3) leads to easily detectable levels of GM-CSF production. In the presence of either heat shock (42° C., 30 minutes; condition 4) or a co-transfected mHSF-1 plasmid (condition 5), GM-CSF production is increased significantly following transfection with the HSE-Tyr 300-GM-CSF plasmid. Co-transfection of a non-melanoma cell line (HT1080) with the HSE-Tyr 300-GM-CSF plasmid and the HSF-1 cDNA did not yield any detectable GM-CSF production (condition 1).

FIG. 7A. Tumor size is presented seven days following injection of CMV-β-Gal, CMV-GALV, or Tyr300-GALV plasmid DNA (10 ug/tumor) into HT1080 tumors in nude mice. FIG. 7B. Same group of mice as in FIG. 7A at 13 days post transduction. FIG. 7C. Same group of mice as in FIG. 7A at 30 days post transduction. FIG. 7D. Size of Me1624 tumors (human melanoma) grown in nude mice at 30 days after injection with CMV-O-Gal, CMV-GALV, or Tyr300-GALV plasmids.

FIG. 9A shows the results of RT-PCR performed to determine the expression of the CAT gene directed by the Tyr 115 base pair promoter, in a range of non-melanoma (lanes 2–9) and melanoma lines (lanes 10–13). FIG. 9B shows the results of a sensitive nested RT-PCR assay to validate the cell type-specific expression of the CAT gene under the control of the Tyr 300 base pair promoter. Lanes are the same as those indicated for FIG. 9A. above).

FIG. 10A is a schematic of a nucleic acid construct according to one embodiment of the invention, where the consensus HSE element (SEQ ID NO:2) is cloned upstream of the Tyr-300 promoter element and is separated from the start of the promoter by a linker (i.e., ACTGGAGAT, SEQ ID NO:7) of either 0 base pair or 10 base pair (i.e., a full turn of the DNA helix) or by 5 base pair (a half turn of the helix). FIG. 10B shows the results of a transient transfection assay using the following constructs: Tyr-300-GM-CSF, HSE-Tyr 300-FULL-GM-CSF, TDE-SV40-GM-CSF, HSF-1d202–316 plasmid, and a construct comprising the HSF-1 cDNA.

FIGS. 13A and 13B show the effects of control (calcium phosphate only) transfections and transfection with CMV-GALV of non-melanoma TelCeB6 cells. FIGS. 13C–D show the effects of transfections of Me1624 cells with the HSE-Tyr-300 and Tyr-300-GALV constructs gave low levels of toxicity when transfected into a melanoma line, (or MeWo, not shown). FIGS. 13E–F show the effects of transfection with increasing amounts of co-transfected HSF-1d202–316 β-Gal plasmid.

FIGS. 14A–C show the effects of different vectors on cell type-specific toxicity of a suicide gene in transfected cells, in this embodiment, a cytotoxic fusogenic protein (GALV). FIG. 14A is a schematic diagram showing the construction of the pBabe-GALV-HSF-1 (HSE-Tyr LTR) vector, pBabe Puro (no GALV nor HSF-1 cDNAs); pBabe-GALV-HSF-1 (wtLTR), pBabe-GALV-HSF-1 (HSE-Tyr LTR), and pBabe-GALV-pBabe Puro vectors. FIG. 14B shows the time course of syncytial development in a melanoma cell line (Me1624) and a non-melanoma cell line (TelCeB6) following infection with viral stocks. The development of syncytia within the cultures was followed at time points following infection (t=0). Syncytia were scored depending upon the proportion of cells in random fields that were within syncytia: −, no visible syncytia; +, 0–20%; ++, 20–40%; +++40–60%; ++++ 60–80%; ++80–100%. FIG. 14C shows the cytotoxicity of the viral vectors of FIG. 14A. At t–120 hrs following infection in the experiment depicted in FIG. 14B above, the total number of surviving cells were counted by trypan blue exclusion.

DESCRIPTION

Figure 1:
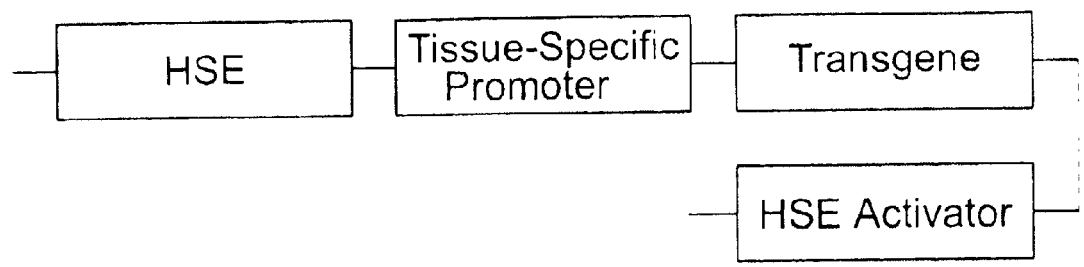
FIG. 1 is a schematic diagram of a nucleic acid construct for the selective expression of a transgene in a target cell according to one embodiment of the invention. "HSE" refs to a heat shock element. The dashed line indicates that the sequence encoding a HSE activator can be optionally included in the same construct with the transgene or in a separate construct.

Tissue specific promoters enable a higher degree of expression of a transgene in certain cells where the transgene product is desired, i.e., in target cells vs. non-target cells. However, in some applications, for example, such as, the delivery of cytotoxic genes to tumor cells, even a low level of expression in non-target cells can be undesirable. The invention provides methods and materials that permit highly selective expression of transgenes in a desired tissue or cell type with little or no expression in non-target cells and tissues. The methods of the invention are useful in the treatment of cancer, genetic disease, and other ailments amenable to gene therapy. The invention is especially useful where selective expression of a transgene in specific target cells with minimal expression in non-target cells is desired for therapeutic or research purposes.

Definitions

In order to more clearly and concisely describe and point out the subject matter of the claimed invention, the following definitions are provided for specific terms which are used in the following written description and the appended claims.

As used herein, the term "nucleic acid molecule" refers to any natural or synthetic nucleic acid, e.g., DNA, RNA, and chemical analogs and derivatives thereof, either single-stranded, or double-stranded, that is capable of encoding an amino acid sequence and serving as a template for synthesis of a polypeptide. As used herein, the term "nucleic acid molecule" encompasses nucleic acid constructs, cassettes, and vectors.

A "nucleic acid construct," "construct," or "cassette" is a nucleic acid molecule which as been assembled from precursor nucleic acid molecules to form a single nucleic acid molecule with a plurality of functions, e.g., a sequence functioning as a promoter plus a sequence functioning to encode a therapeutic gene. As used herein, the term "construct" encompasses the term "vector."

A "vector" is a nucleic acid molecule which is suitable for introduction of a nucleic acid construct or transgene into a target cell by transfection or transformation. Vectors of the invention include, but are not limited to, any plasmid vector or viral vector known in the art.

A "target cell" is any cell which is the preferred or intended recipient of a nucleic acid construct or transgene which can be delivered either in vivo or ex vivo, including human cells.

A "transgene" is any nucleic acid sequence that encodes a polypeptide for expression in a target cell.

A "therapeutic transgene" is a transgene encoding a protein which achieves a therapeutic effect when expressed in a cell. A "therapeutic effect" is an effect which ameliorates the symptoms of a disease or which restores molecular parameters to normal levels, i.e., restoring the expression of genes and/or proteins and/or other biomolecules to a level found in individuals who do not have the disease. For example, in one embodiment, the therapeutic effect in a patient with prostate cancer is the restoration of PSA levels to within normal levels (no significant difference determined between levels of PSA in the patient with prostate cancer compared to a patient without prostate cancer, as determined by routine statistical testing to within 95% confidence levels).

A "cytotoxic gene" is any nucleic acid sequence that leads to the death of a cell in which it is expressed within a period of 1, 2, 3, 5, 7, 10, 14, 21, 30, 60, or 100 days.

A "cell type-specific" promoter, promoter element, enhancer, or enhancer element according to the invention is one which leads to a higher degree of expression of a gene under its control in a target cell of the cell type in which the promoter is active than in a non-target cell of 3, cell type in which the promoter is substantially inactive. A promoter, promoter, promoter element, enhancer, or enhancer element, is preferably highly cell-type specific, in which case, the "specificity of expression" of the gene under their control is at least 5-fold, 7-fold, 8-, 9-, 10-, 20-, 30, 50–100-, 300-, 1000-, 3000-, 10,000-, 30,000-, or 100,000-fold higher in a specific cell type/target cells than in non-target cells. Since non-target cells may differ with respect to expression of a given promoter, promoter element, enhancer, or enhancer element, an average of the expression in at least five different non-target cell types should be compared with the expression in target cells to determine the specificity of expression. A cell type-specific promoter encompasses both tissue-specific promoters and tumor-specific promoters. In one embodiment, the cell-type specific promoter is both tissue-specific and tumor-specific.

As used herein, the terms "promoter element" refers to a subsequence of a promoter that binds to a transcriptional activator. As used herein, the term "promoter element" encompasses enhancer sequences.

An "enhancer" is a sequence which enhances transcription of a promoter and which can be placed in any orientation with respect to the promoter and can function upstream or downstream of a gene, to enhance transcription.

A defined herein, "operably linked" refers to a promoter sequence or promoter element or enhancer which is in sufficient proximity to the transcription start site of a gene to regulate transcription of the gene.

An "amplification promoter element" refers to a sequence, which activates transcription of an operably linked sequence in the presence of an amplification promoter transcription activator. In one embodiment, an amplification promoter element is a heat shock element (HSE) activateable by a "heat shock activator". A heat shock activator is a transcription activator which is expressed or activated when a cell is exposed to heat or other environmental stressors.

A "transcription activator" is a biomolecule (e.g., protein, polypeptide, nucleic acid sequence, and the like) which binds to a promoter element and enhances transcription of an operably linked gene as compared to the transcription of the gene in the absence of the transcription activator.

Cell Type-Specific Promoters

In one embodiment of the invention, highly cell type-specific promoters are screened for to drive the expression of a therapeutic transgene in a target cell of interest (e.g., a specific tissue or tumor cell). In one embodiment, the cell type-specific promoter is identified by validating that the cell-type specificity of a known cell type-specific promoter when cloned upstream of a therapeutic transgene provides expression of the transgene at levels which are 5-fold, 7-fold, 8-, 9-fold, 10-fold, 20-fold, 30-fold, 50-fold, 100-fold, 300-fold, 500-fold, 1000-fold, 3000-fold. 10,000-fold, 30,000-fold, or 100,000-fold higher in the specific cell type (e.g., the target cell) than in cells which are other than the specific cell type (e.g., non-target cells), after evaluating gene expression in at least six different types of cells or tissue types. In one embodiment, a highly cell type-specific promoter is identified which is expressed in only one of the at least six tissues examined. In another embodiment, the cell type specific promoter provides expression of the transgene at levels which are at least 100-fold, at least 500-fold, or at least 100-fold higher in the specific cell type than in cells which are other than the specific cell type.

In another embodiment of the invention, novel or uncharacterized sequences are screened to identify highly cell type-specific promoter sequences. In another embodiment, minimal promoter sequences are identified, e.g., the minimum length of sequence necessary and sufficient to drive highly cell type-specific expression of a transgene in amounts necessary to achieve a therapeutic effect.

Identification of Known Cell Type-Specific Promoters

In one embodiment of the invention, selective expression of a therapeutic transgene for delivery into a cell (either in vivo or ex vivo) is achieved by placing the transgene under control of a highly cell type-specific promoter, which is identified by searching the published literature and/or sequence databases. In one embodiment, the cell type—specific promoter is a tissue-specific promoter. Examples of promoters with high tissue specificity that have been reported include, but are not limited to, the promoters for tyrosinase (specific for melanoma cells and melanocytes; Bentley, et al. Mol. Cell. Biol. 14: 7996–8006 (1994)), carcinoembryonic antigen (CEA, specific for colorectal cancer cells; Schrewe, et al. Mol. Cell. Biol. 10: 2738–2748 95 (1990)), alpha fetoprotein (hepatocytes; Ghebranious, et al. Mol. Reprod. Dev; 42: 1–6 (1995)), erb-B2 (breast cancer; Pandha, et al., J. Clin. Oncol. 17: 2180(1999)), and myelin basic protein (glioma cells; see Shinoura, et al. Cancer Res. 59: 5521–5528 (1999)).

Additional examples of cell type-specific promoters include, but are not limited to, $\alpha$-S 1- and $\beta$-casein promoters which are specific for mammary tissue (Platenburg, et al., Trans. Res. 3: 99–108 (1994); Maga, et al., Trans. Res. 3: 36–42 (1994)); the phosphoenolpyruvate carboxykinase promoter, which is active in liver, kidney, adipose, jejunum and mammary tissue (McGrane, et al., J. Reprod. Fert. 41: 17–23 (1990)); the involucerin promoter, which is only active in differentiating keratinocytes of squamous epithelium (Carroll, et al., J. Cell Sci. 103: 925–930 (1992)); and the uteroglobin promoter, which is active in lung and endometrium (Helftenbein, et al., Annal. N.Y. Acad. Sci. 622: 69–79(1991)).

The near completion of the human genome project has resulted in sequence data relating to the structure of many additional cell type-specific promoters being available to the public. In one embodiment, therefor, a cell type-specific sequence to be used in generating a construct according to the invention is obtained from a database such as the Eukaryotic Promoter Database (EPD) [[(http://www.epd.isb-sib.ch/)]]. The sequences included within this database (and other sequence databases) and which are added to these databases are encompassed within the scope of the invention.

In certain embodiments of the invention, the highly cell type-specific promoter is a tumor-specific promoter which drives the expression of the transgene in tumor cells but does not significantly express the transgene in non-tumor cells. In a preferred embodiment, a highly tumor-specific promoter expresses a transgene to which it is operably linked greater than 100-fold, greater than 500-fold, or greater than 1000-fold in tumor cells compared to non-tumor cells. Tumor-specific promoters encompassed within the scope of the invention include, but are not limited to, promoters which control the expression of prostate specific antigen or PSA (Osterling, J. Urol. 145: 907–923 (1991)), epithelial membrane antigen, expressed in multiple epithelial carcinomas (Pinkus, et al;. Am. J. Clin. Pathol. 85: 269–277 (1986)), CFYRA 21-1, expressed in lung cancer (Lai, et al., Jpn. J. Clin. Oncol. 29: 421 (1999)) and Ep-Cam, expressed in pan-carcinoma cells (Chaubal, et al., Anticancer Research 19: 2237–2242 (1999)). The entireties of these references are incorporated by reference herein.

Identification of New Cell Type-Specific Promoter Sequences

Elements of promoters or enhancers can be identified which will selectively drive the expression of a transgene in a desired target cell using methods which are standard in the art. For example, in one embodiment, a gene is identified which is expressed in a cell type-specific manner by obtaining a subsequence of the gene (or cDNA) for use as a probe or primer (e:g., from a genomic or cDNA library), and determining whether the gene is expressed in one or a few cell types (e.g., one or a few tissues and/or tumor types). In one embodiment, the subsequence is used as a probe and its hybridization to RNA or cDNA obtained from one cell type, and lack of hybridization in at least five other cell types, is used to identify the gene as one whose expression is cell type-specific. In another embodiment, cell type-specificity of a promoter is detenrmined by monitoring the expression of the protein product of the gene, for example, by immunoassay, or any other protein detection method. In one embodiment, tissues are obtained from patients, from autopsy specimens, or from commercially available sources (e.g., such as Clontech's "Tissue Northems"). In another embodiment of the invention, tumor-specific promoters are identified by examining the expression of the protein product in tumor cell lines, biopsy samples, and other sources of tumor tissue, and comparing this expression to the expression in non-tumor cells.

Having a identified a gene expressed in a cell type-specific specific manner, a cell type-specific or tumor-specific promoter sequence from this gene is then identified from genomic clone(s) and the ability of the promoter sequence to drive the expression of a transgene in a cell type-specific manner is determined.

Defining Minimal Promoter Sequences

Methods of identifying promoter sequences are routine in the art. For example, in one embodiment of the invention, to identify a promoter sequence, the 5' portion of a gene is analyzed for the presence of sequences characteristic of promoter sequences, such as a TATA box consensus sequence (TATAAT), which is usually an AT-rich stretch of 5–10 base pair located approximately 20 to 40 base pair upstream of the transcription start site. In one embodiment, the location of a TATA box is determined using standard RNA-mapping techniques such as primer extension, S1 analysis, and/or RNase protection, to identify the position of the transcription start site within a genomic clone, and the TATA box is identified, either visually, or using a sequence search program. For example, sites important in transcriptional activation can be identified using the publicly available sequence search program TF SEARCH. Another publicly available database of sequences to which transcription factors bind is available from the National Library of Medicine in the "Transcription Data Base."

To define a minimal cell type-specific promoter sequence, sequences upstream of the transcription start site are fused to a reporter gene (e.g., beta-galactosidase, luciferase, chloramphenicol acetyltransferase or CAT, green fluorescent protein or GFP, and the like) in order to determine which sequences are both necessary and sufficient to drive expression of the reporter gene. If sequences are identified which contain the necessary sequences for cell-type specific expression (e.g., tissue-specific and/or tumor-specific), deletions can be made in the 5' flanking sequences of a genomic clone to determine which sequences are minimally required for tissue-type specific expression. This can be performed ex vivo, first, by examining the expression of the reporter gene operably linked to the flanking sequences in cell type-specific culture cells, with comparison to expression in non-cell type-specific culture cells, e.g., using primary cell lines obtained from different tissue types or continuous cell lines known to express the properties of specific tissue types, or tumor cell types (such as obtainable from the American Type Culture Collection ATCC®; Manassas, Va.

In one embodiment, to verify that a nucleic acid molecule (e.g., construct and/or vector) is successfully expressing a desired transgene in a cell type-specific manner in vivo, the cell type-specific promoter is cloned upstream of the transgene of interest and the transgene is introduced into a mammal (e.g., a mouse, such as the C57BL/6J strain, or a rat) using standard techniques (see, e.g., "Manipulating the Mouse Embryo" by Brigid Hogan, Frank Costantini and Elizabeth Lacy, Cold spring Harbor Laboratory, Cold Spring Harbor, N.Y., the entirety of which is incorporated herein by reference). In one embodiment, the nucleic acid molecule, construct, or vector is introduced into the pronucleus of fertilized mouse oocytes according to standard kit procedures.

For example, in one embodiment, mouse zygotes are collected from six week old C57B/6J females (Jackson Laboratory, Bar Harbor, Me.) that have been superovulated with 5 IU of Pregnant Mare's Serum Gonadotropin followed 48 hours later by 50 U Human Chorionic Gonadotropin. Primed females are placed with C57BL/6J males and checked for vaginal plugs the following morning. Pseudopregnant females, used as recipients, are selected for estrus and placed with proven sterile vasectomized males.

Zygotes are collected (e.g., in BMOC-2 medium modified to contain 5.1 g/l NaCl and 5 mg/ml bovine serum albumin) and cumulus cells are removed by treatment with hyaluronidase (e.g., Sigma Type IV, 300 IU/ml PBS with 1% PVP 40T, Sigma) diluted to 60 IU/ml in culture medium. Zygotes are washed several times in culture medium to remove debris. Approximately 2 pl of DNA solution (1–2 ng DNA/ IA of buffer) is injected into zygotes which are incubated in 5% $CO_2$ in air at 37° C. until transferred to the oviduct of recipient females under a suitable anaesthesia (see, e.g., as described in Brinster, et al., Proc. Natl. Acad. Sci. USA 82: 4438 (1985), the entirety of which is incorporated herein by reference). While injection can be done in fertilized oocytes, transgenic animals can be obtained from injected two-cell embryos. Transferred oocytes/embryos are allowed to differentiate and develop within the recipient females.

Increased efficiency of integration into the genome can be achieved by linearizing the nucleic acid molecule prior to injection, and by injection into the male or female pronucleus of the oocyte rather than the cytoplasm. The strain of mouse can also be optimized to enhance efficiency of integration. For example, in addition to C57BL6 mice, hybrid C57xSJL mice or CD-1 mice can also be used.

Transgenic founder mice carrying single copies of the therapeutic transgene under the control of a highly cell type-specific promoter are screened and selected by analyzing a source of genomic DNA (e.g., a section of tail or ear). In one embodiment, the therapeutic transgene is r: injected into the oocyte/embryo of a mouse null for the therapeutic transgene, in which case, the copy number and structure of the transgene which is integrated into the genome is analyzed by hybridization with nucleic acids from the transgene to determine whether any rearrangement or modification has occurred in the transgene during the integration process. However, when a null background is not used, the presence and structure of a reporter gene which is part of the same molecule as the therapeutic transgene is ascertained. Only mice carrying single copies of the complete transgene/ reporter gene are selected for analysis of cell type-specific gene expression. In one embodiment, both the therapeutic transgene and reporter gene are operably linked to the same cell type-specific promoter.

Transgenic founder mice (e.g., expressing a marker gene cloned on the same molecule as the therapeutic transgene) are analyzed using any known assay to either quantitatively or semi-quantitatively indicate the level of expression of the transgene in target cells or tissue compared with non-target cells or tissue. For example, reverse transcriptase polymerase chain reaction (RT-PCR) can be used to quantify the amount of mRNA produced by a target cell after delivery of the transgenes (see, e.g., Vile, et al., Virology 214: 307–313 (1995)). Alternatively, a reporter gene can be included in the nucleic acid molecule, construct, or vector, and the reporter gene product can be quantified using available techniques such as immunoassay, fluorescence, spectroscopy, and the like.

In one embodiment, appropriate tissues are collected at autopsy from transgenic mice to assay for expression of the therapeutic transgene and/or reporter gene. RNA and/or protein are extracted from these tissues and used in hybridization assays and/or immunoassays to detect expression of transgene/reporter mRNA and/or protein. In one embodiment, tissues are selected from brain, skin, liver, spleen, kidney, heart, lung, gonad, uterus, pancreas, fundus of the stomach, duodenum, ileum, colon and sternal bone marrow to perform RT-PCR, in situ hybridization and/or immunohistochemistry.

The specificity of expression of a transgene under the control of a cell type-specific promoter can be evaluated by comparing expression of the transgene using any of the above methods in a target cell (e.g., the specific cell type) with the expression in non-target cells. Since non-target cells may differ with respect to expression of a given promoter or enhancer, in one embodiment, an average of the expression in at least five different non-target cell types is compared with the expression in target cells to determine the specificity of expression.

Melanoma-Specific Promoters

In one embodiment, the invention comprises nucleic acid constructs in which the cell type-specific promoter controlling the expression of the therapeutic transgene is the minimal melanoma-specific promoter of 300 base pair corresponding to bases –300 to –1 of the human tyrosinase gene ("Tyr300"; SEQ ID NO: 1):

| (–300) | tcatttgcaa | ggtcaaatca | tcattagttt | tgtagtctat |
|---|---|---|---|---|
| | taactgggtt | tgcttaggtc | aggcattatt | attactaacc |
| | ttattgttaa | tattctaacc | ataagaatta | aactattaat |
| | ggtgaataga | gtttttcact | ttaacatagg | cctatcccac |
| | tggtgggata | cgagccaatt | cgaaagaaaa | gtcagtcatg |
| | tgcttttcag | aggatgaaag | cttaagataa | agactaaaag |
| | tgtttgatgc | tggaggtggg | agtggtatta | tataggtctc |
| | agccaagaca | tgtgataatc(–1) | | |

Tyr300 is a subsequence of the 5' untranslated region of the human tyrosinase gene whose sequence was previously described by Bentley, et al., Mol. Cell. Biol. 14:7996–8006 (1994), the entirety of which is incorporated by reference herein. The 300 base pair element of the human tyrosinase promoter contains at least four positive DNA binding elements as well as one negative element as described by Bentley et al, supra. Of particular importance is the M box (at –107 to –97), a conserved element found in other melanocyte-specific promoters (Bentley, et al., supra).

In one embodiment, Tyr300 is incorporated into a recombinant construct where it functions as a highly selective activator for transgene expression in melanoma cells (see Example 1).

Other melanoma-associated polypeptides are known and their genes can be screened to identify the presence of melanoma-specific promoters, as described above. These polypeptides are described in, for example, Kupsch, et al., Hum. Gene Ther. 9: 737–746 (1998); Neri, et al., J. Invest. Dermatol. 107: 164–170 (1996); and Kirkin, et al., Exp. Clin. Immunogen. 15: 19–32, (1998), the entireties of which are incorporated by reference herein.

Amplification of Cell Typespecific Promoter Activity

In selecting for promoter elements with high cell type-specificity, the inventors discovered that the such promoters tend to be weaker than promoters which mediate less selective expression of downstream sequences, i.e., cell type-specificity is achieved at the expense of promoter strength. Therefore, in one embodiment, methods and materials with which to drive tissue-selective expression of transgenes using a positive feedback mechanism are provided.

In one embodiment according to the invention, an amplification promoter element, such as a heat shock element is used to amplify the expression of a downstream therapeutic transgene. Heat shock elements ("HSEs") are sequences found within the first 100 base pair 5' of the RNA start site of eucaryotic heat shock genes (see, e.g., Sorger, P. K. Cell 65:363 (1991), the entirety of which is incorporated by reference herein). Heat shock genes, such as Hsp70 genes, from different species differ in the number and orientation of HSEs and in the types of other transcription factor-binding sites found upstream. HSEs include the sequence nGAAn, repeated at least two times in head-to-head or tail-to-tail orientation (nGAAnnTTCn (SEQ ED NO5 or nTTCn-nGAAn (SEQ ID NO:6)), and in one embodiment of the invention, the HSE comprises at least two nGAAn sequences.

An HSE functions in stress-induced promoter activation by binding a positive transactivating factor, the heat shock factor (HSF-1). The binding constant of this factor to the heat shock element is about a hundred-fold higher than that of any other known mammalian transcription factor to its respective binding site, rendering it a very strong promoter element. The present invention provides a strategy to amplify the expression of a transgene by providing at least-one upstream HSE, responsive to an HSF. This strategy can be applied to augment the activity of any promoter and consequently boost the expression of any transgene.

HSE is inducible by HSF-1 in the presence of environmental stressors such as heat, Fad anoxia, or ethanol. Therefore, in one embodiment, a target cell is exposed to heat during and/or prior to, and/or after delivery of a therapeutic transgene whose expression is mediated by an HSE Ielement activated by an HSF-1. Heat activates the HSF-1 protein and allows it to enter the nucleus and bind HSE. In one embodiment, "cxposing the target cell to heat" comprises elevating the temperature of the target cell, either by localized heating, e.g., that which may be produced by a focused microwave beam, or by generalized heating, e.g., by a temperature bath. In one embodiment of the invention, the production of the therapeutic transgene's product is enhanced by increasing the ambient temperature of the cells to which is has been/ or is being delivered, to a temperature above 37° C. In another embodiment, cells are maintained at a temperature of 38 to 45° C., more preferably 39 to 44° C., and most preferably 40 to 43° C., for a period of 1 to 12 hours, more preferably 4 to 6 hours, and most preferably 6 hours. In another embodiment, the temperature is elevated periodically, i.e., for 1 to 10 hours a day, more preferably 3 to 6 hours a day, for a period of 1 to 21 days or more.

Other suitable temperatures and time periods can be readily determined by one of skill in the art to optimize the efficiency of the HSE, thereby maximizing production levels of a desired therapeutic transgene product. The induction of HSE's in human cells is described further in Ritossa, Experientia (Basel) 18: 571 (1962); Nover, *Heat Shock of Eukaryotic Cells* Springer, Berlin (1984); Craig, CRC Cit. Rev. Biochem. 18: 239 (1985); Pelham, Trends Genet. 1: 31 (1985); Lindquist, Ann. Rev. Biochem. 55: 1151 (1986); Pelham, et al., EMBO J., 1: 1473 (1982); Mirault, et al., EMBO J. 1: 1279 (1982); Wu, et al., Mol. Cell. Biol. 5: 330 (1985); Voellmy, et al., Proc. Natl. Acad. Sci. USA 82: 4949 (1985); Drabent, et al., Nucl. Acids Res. 14: 8933 (1986); Berger, et al., Somat. Cell. Molec. Genet. 12: 433 (1986); Wu, et al., Proc. Natl. Acad. Sci. USA 83: 629 (1986), for example, the entireties of which are incorporated herein by reference.

Chemical agents can also be used to induce the HSE, e.g., through their interactions with HSF-1 (see, e.g., as described in U.S. Pat. No. 5,137,805, the entirety of which is incorporated by reference herein). Activators of HSF-1, such as activating antibodies, polypeptides, and peptide fragments, or aptamers, can be introduced by providing their sequences along with those of the therapeutic transgene and the HSF-1, or by administering the activator directly to the patient (e.g., intravenously, intramuscularly, subcutaneously, enterally, or parenterally), by continuous infusion, or by single or multiple boluses. This is preferred when the activator is a drug rather than a polypeptide. The activation of the heat shock element by any of the stressors described above provides synergistic immunotherapeutic effects caused by the induction of heat shock proteins (encoded by sequences which also comprise HSE's), which are stimulated by the rise in HSF-1.

Alternatively, a sequence encoding a constitutively active mutant of HSF-1 can be employed (see Example 2), in which case no heat activation step is required. This embodiment may be used where delivery of the transgenes is performed in vivo rather than ex vivo.

In one embodiment, an HSE sequence is positioned upstream (5' of) a cell type-specific promoter element that regulates the expression of the therapeutic transgene. In another embodiment, multiple HSE sequences are provided. In one embodiment, an HSF-1 sequence is provided as part of a separate nucleic acid construct. In this embodiment, the construct comprising the therapeutic transgene and the construct encoding the HSF-1 protein are provided sequentially, either within minutes or hours of each other; while in a preferred embodiment, the construct comprising the therapeutic transgene and the construct encoding the HSF-1 protein arc be delivered to a cell simultaneously, e.g., in the same pharmaceutical excipient.

In another embodiment, the therapeutic transgene and the HSF-1 encoding sequence are part of the same nucleic acid construct and the transcription of both genes is controlled by the upstream HSE and a cell type-specific promoter. While the low level of promoter activity from the cell type-specific promoter initially supports only a low level of transcription of both transgenes, eventually HSF-1 accumulates to a level which activates the HSE and thereby increases transcription of both the therapeutic transgene and the HSF-1.encoding gene. This positive feedback loop converts a highly specific, but low level of promoter activity, into a highly specific and strong level of promoter activity in a target cell for which the promoter was designed.

Figure 6:
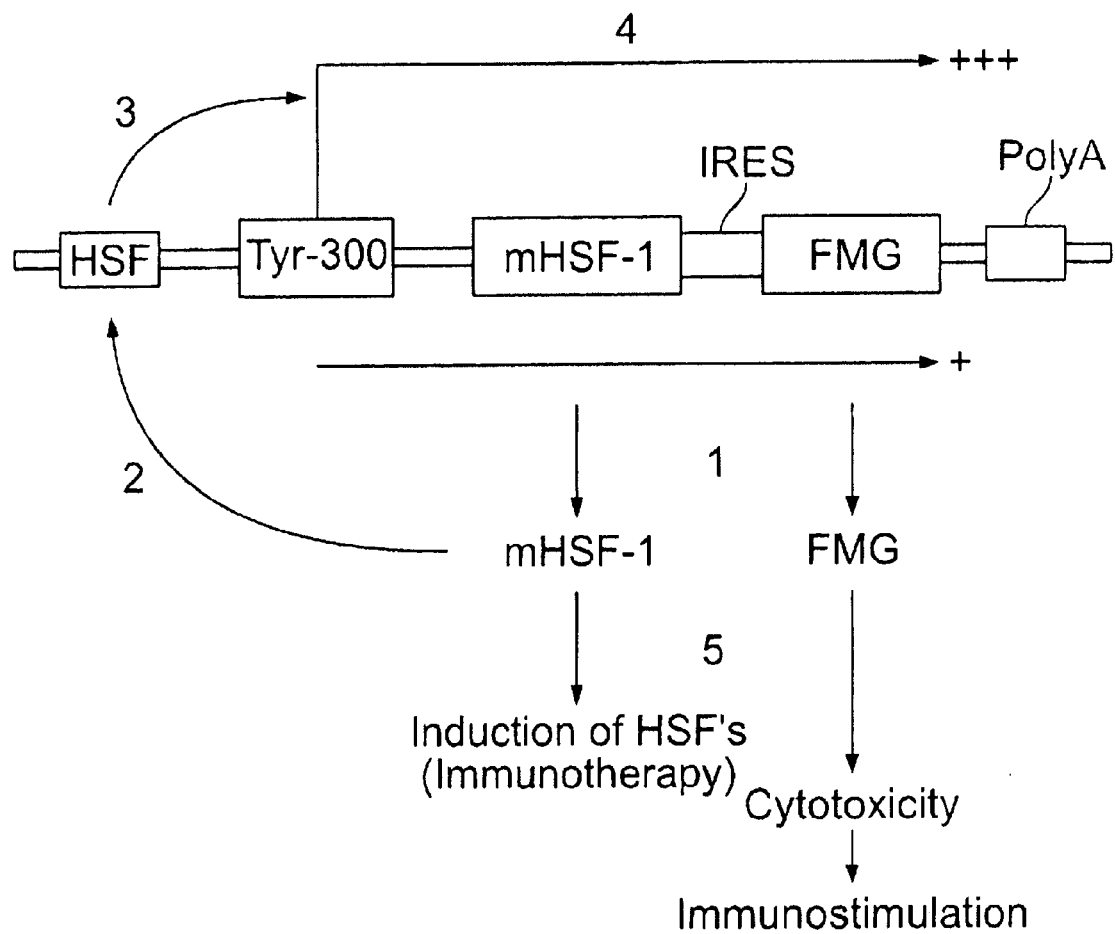
FIG. 6 displays a portion of an expression vector in which an HSE transcriptional control element can be used to transactivate gene expression from the melanoma-specific Tyr-300 promoter. (FMG: fusogenic membrane glycoprotein; IRES: internal ribosomal entry site).

A construct which exemplifies this approach is depicted in FIG. 6. In this embodiment, a nucleic acid molecule embodying this method comprises: (1) an HSE sequence such as the human consensus sequence 5'-AGAATGTTCTAGAAG-3' (SEQ ID NO:2, see Zuo, et al., Mol. Cell. Biol. 15: 4319–4330 (1995)); which is placed upstream of (2) any promoter, and which is followed in a 3' direction by (3) a transgene whose expression is desired, which turn is followed in a 3' direction by (4) a sequence that encodes a transcription factor or transcriptional activator that binds to and activates HSE, such as human heat shock factor-1 (HSF-1). The order of the transgene and the sequence encoding the transcription factor is unimportant; either gene can be positioned near the promoter, as long as transcription of both coding sequences is driven by the promoter. Where HSF-1 in encoded by a sequence not under control of HSE, then simple amplification of expression of the transgene under control of HSE will result.

In another embodiment, an internal ribosomal entry site (IRES) is placed between the therapeutic transgene and the HSF-1 encoding sequence, so that both the product of the therapeutic transgene and the HSF-1 protein are translated from the same message. Internal ribosome entry sites (IRES, also called ribosomal landing pads) are sequences that enable a ribosome to attach to mRNA downstream from the 5' cap region and scan for a downstream AUG start codon, for example in polycistronic mRNA. See generally, Miles, et al., U.S. Pat. No. 5,738,985 and N. Sonenberg and K. Meerovitch, Enzyme 44: 278–91 (1990), the entireties of which are incorporated herein by reference. Addition of an IRES between the coding sequences for two transgenes, for example, a cytotoxic gene and a gene encoding HSF-1, can enable the independent translation of either the transgene or HSF-1 from a dicistronic or polycistronic transcript.

IRES sequences can be obtained from a number of RNA viruses (e.g., picornaviruses, hepatitis A, B, and C viruses, and influenza viruses) and DNA viruses (e.g., adenovirus). IRES sequences have also been reported in mRNAs from eukaryotic cells (Macejak and Sarnow, Nature 353: 90–94 (1991) and Jackson, Nature 353: 14015 (1991)). Viral IRES sequences are detailed in the following publications: (a) Coxsackievirus: Jenkins, J. Gen. Virol. 68: 1835–1848 (1987); Iizuka, et al., Virology 156: 64–73 (1987); and Hughes, et al., S. Gen. Virol. 70: 2943–2952; (b) Hepatitis A Virus: Cohen, et al., Proc. Natl. Acad. Sci. USA 84: 2497–2501 (1987); and, Paul, et al., Virus Res. 8: 153–171 (1987); (c) *Poliovirus*: Racaniello and Baltimore, Proc. Natl. Acad. Sci. USA 78: 4887–4891 (1981); and Stanway, et al., Proc. Natl. Acad. Sci. USA 81: 1539–1543 (1984); (d) *Rhinovirus*: Deuchler et al., Proc. Natl. Acad. Sci. USA 84: 2605–2609 (1984); Leckie, G., Ph.D. thesis, University of Reading, UK; and Skem, et ¢. al., Nucleic Acids Res. 13: 2111 (1985); (e) Bovine enterovirus: Earl et al., J. Gen. Virol. 69: 253–263 (1988); (f) *Enterovirus* type 70, Ryan, M. D. et al., S. Gen. Virol. 71: 2291–99 (1989); (g) Theiler's murine encephalomyelitis virus: Ohara, et al., Virology 164: 245 (1988); and, Peaver, et al., Virology 161: 1507 (1988); (h) Encephalomyocarditis virus: Palmenberg, et al., Nucl. Acids Res. 12: 2969–2985 (1984); and Bae, et al., Virology 170: 282–287 (1989); (i) Hepatitis C Virus: Inchauspe, et al., Proc. Natl. Acad. Sci. USA 88: 10293 (1991); Okamoto, et al., Virology 188: 331–341 (1992); and Kato, et al., Proc. Natl. Acad. Sci. USA 87: 9524–9528 (1990); and (i) Influenza virus: Fiers, W., et al., Supramol. Struct. Cell Biochem. (Suppl 5): 357 (1981), the entireties of which are incorporated herein by reference.

In other embodiments, other stress inducible promoter elements and stress inducible transcriptional activators, in addition to HSEs and HSFs, respectively, can be used and are encompassed within the scope of the invention. Examples of such types of promoter elements and the activators which regulate them are described in Davis, J. Biol. Chem. 268: 1553 (1993); Holbrook, et al., in: *Stress-Inducible Cellular Responses*, Feige, U., et al., Eds., Birkhauser Verlag (1996); Datta, et al., Proc. Natl. Acad. Sci. USA, 89(21): 10149–10153 (1992); Datta, et al., Proc. Natl. Acad. Sci. USA, 90(6): 2419–2422, (1993); Alexandropoulos, et al., Nucleic Acids Research, 20(9): 2355–2359 (1992); Attar, et al., Molecular and Cellular Biology, 12 (5): 2432–2443, (1992); S. Qureshi, et al.; The Journal of Biological Chemistry, 266(17): 10802–10806 (1991); U.S. Pat. No. 6,034,228; U.S. Pat. No. 5,827,685; and U.S. Pat. No. 5,770,581, and in U.S. Provisional Application Ser. No. 60/193,977, filed Mar. 31, 2000, the entireties of which are incorporated by reference.

As with the HSE-HSF "circuit," the stress-inducible promoter elements described above can be activated by exposing the target cell to the appropriate stressor, which in turn activates the transcription activator, or alternatively, by rendering the expression of the stress-activated transcriptional activator constitutive, e.g., by site-directed or random mutagenesis of the stress activated transcriptional activator and by screening for constitutive activators in cell lines, for example. Amplification promoter elements encompassed generally within the scope of the invention include any promoter element or enhancer sequence responsive to a transcriptional activator which when operably linked to a therapeutic transgene, which in turn is under the control of a highly cell type specific promoter, is capable of driving expression of the transgene at levels suitable for achieving a therapeutic effect.

Transgenes for use in the Nucleic Acid Constructs

The nucleic acid molecules, constructs, and vectors of the invention can employ any desired transgene for delivery to, and expression in, a target cell. In one embodiment, the transgene encodes for a protein product whose presence is desired in the target cell for therapeutic, investigational, or other purposes. For example, in one embodiment, the transgene encodes a protein which is defective in, or absent from, the target cell because of genetic disease or a pathological condition.

Genes and the diseases associated with them that are appropriate targets for gene therapy using the methods of the invention include, but are not limited to: AGA aspartylglucosaminidase (GenBank Acc. No. X55330), aspartylglucosaminuria; ALDOB aldolase B, fructose-bisphosphate (GenBank Acc. No. X02747), fructose intolerance; BLM Bloom syndrome (GenBank Acc. No. U39817), Bloom syndrome; CFTR cystic fibrosis transmembrane conductance regulator (GenBank Acc. No. S64699), cystic fibrosis; CLCN1 chloride channel 1, skeletal muscle (GenBank Acc. No. Z25884), Thomsen disease; CRH corticotropin releasing hormone (GenBank Acc. No. V00571), ACTH deficiency; DBH dopamine beta-hydroxylase (GenBank Acc. No. X13255), Dopamine-beta-hydroxylase deficiency; FI 1 coagulation factor XI (plasma thromboplastin antecedent) (GenBank Acc. No. M13 142), Factor XI deficiency; GAA glucosidase, alpha, acid (GenBank Acc. No.X55079), glycogen storage disease II; GALC galactosylceramidase (GenBank Acc. No. D86181), Krabbe disease; GALT galactose-1-phosphate uridylyltransferase (GenBank Acc. No. M1873 1), galactosemia; HBB hemoglobin, beta (GenBank Acc. No.V00497), sickle cell anemia (beta-thalassemia); HD huntington (GenBank Acc. No. L12392), Huntington disease; FTL ferritin, light polypeptide (GenBank Acc. No. MI 11147), hyperferritinemia-cataract syndrome; MAOA monoamine oxidase A (GenBank Acc. No.M68840), Brunner syndrome; MATIA methionine adenosyltransferase I, alpha (GenBank Acc. No. D49357), hypermethioninemia; PAH phenylalanine hydroxylase (GenBank Acc. No. U49897), phenylketonuria; PROS1 protein S (alpha) (GenBank Acc. No. M14338), protein S deficiency; OA1 ocular albinism (GenBank Acc. No. Z48804), Nettleship-Falls type; SGSH N-sulfoglucosamine sulfohydrolase (sulfamidase) (GenBank Acc. No. NM000199), Sanfilippo syndrome, type A; CCND1 cyclin D1 (PRAD1: parathyroid adenomatosis 1) (GenBank Acc. No. X59798); parathyroid adenomatosis 1, centrocytic lymphoma; DMD dystrophin (GenBank Acc. No. X15149), muscular dystrophy, Duchenne.

Cytotoxic Transgenes which Provide an Immunostimulatory Component

Gene therapy designed to eradicate tumors has benefited from strategies for simultaneously killing the tumor cells and stimulating the immune response. For example, tumor cell death induced by the HSV thymidine kinase/gancyclovir system also induces hsp70 expression, which in turn induces infiltration of T-cells, macrophages, and dendritic cells, and also increases the expression of cytokines (see, e.g., Todryk, et al., J. Immunol. 163: 1398–1408 (1999)). Infection by replication-competent adenovirus present in adenoviral vectors also induces hsp70 expression and therefore stimulates an immune response to the delivery of cytotoxic transgenes (Melcher, et al., Hum. Gene Ther. 10: 1431–1442 (1999)). Another approach to enhance the immunogenicity of tumors is to provide hsp70 directly to the cells (e.g., by transfecting them with cDNA encoding hsp 70 as described in Melcher, et al., Nat. Med. 4: 581–587 (1998), for example). The entireties of these references are incorporated herein by reference.

In one embodiment, a transgene for use with the invention is a cytotoxic gene or suicide gene that is intended to selectively destroy the target cell. Examples of cytotoxic genes include GAL Venv (e.g., Genbank Acc. No. M26927), HSVTK (e.g., Genbank Acc. Nos. AF057310, X01712), cytosine deaminase (e.g., Genbank Acc. No. S56903), nitroreductase (e.g., Genbank Acc. No. A23284), or VSV glycoprotein G (e.g., Genbank Acc. No. X03633).

In one embodiment of the invention, a therapeutic transgene according to the invention, encodes a protein with both direct cytotoxic and immunostimulatory properties (e.g., fusogenic proteins) which is cloned downstream of a cell type-specific promoter and an HSE. One example of such a protein is the fusogenic membrane glycoprotein (FMG) (Batinan, et al., Cancer Res. 60: 1492–1497 (2000); Diaz, et al. Gene Three. 2000; In press; Fielding, et al., Hum Gene Three. 11: 817–826 (2000). FMGs kill tumor cells by causing fusion between cells expressing the FMG and neighboring cells which express the receptor for the FMG.

The fusogenicity of fusogenic proteins means that large local bystander effects can be achieved, where non-expressing cells can be recruited into large multi-nucleated syncytia and eventually killed. Indeed, the bystander killing of an FMG in vitro is at least one log higher than that of the conventional suicide genes, HSVtk or CD, in most tumor cell lines tested so far (Bateman, et al., supra). In addition, expression of viral FMG is also highly immunostimulatory as judged by the immunogenicity of FMG-expressing vaccines and by the induction of stress related proteins such as inducible heat shock proteins during the killing process (Bateman, et al., supra, Diaz, et al., supra). These dual properties of high local killing capacity and immunostimulatory activity make fusogenic proteins attractive transgene products for use in gene therapy of cancer.

Fusogenic proteins are known in the art and include, but are not limited to, viral FMGs such as type G membrane glycoproteins of rabies virus, Mokola virus, vesicular stomatitis virus, and Togavirues, as well as murine hepatitis virus JHM surface projection protein, porcine respiratory coronavirus spike glycoprotein, porcine respiratory coronavirus membrane glycoprotein, avian infectious bronchitis spike glycoprotein and its precursor, bovine enteric coranavirus spike protein, paramyxovirus SV5 F protein, Measles virus F protein, canine distemper virus F protein, Newcastle disease virus F protein, human parainfluenza virus 3 F protein, simian virus 41 F protein, Sendai virus F protein, human respiratory syncytial virus F protein, Measles virus hemagglutinin, simian virus 41 F protein, Sendai virus F protein, human respiratory syncytial virus F protein, Measles virus hemagglutinin, simian virus 41 hemagglutinin neuramnimidase proteins, human parainfluenza virus type 3 hemagglutinin neuramidase, Newcastle disease virus neuramidase, human herpesvirus 1 gB, simian varicella virus gH, human herpesvirus gB proteins, cercopithecine herpesvirus gB proteins, Friend murine leukemia virus envelope glycoprotein, influenza virus hemagglutinin, poxvirus membrane glycoprotein, Russian Far East encephalitis virus membrane glycoprotein, Venezuelan equine encephalitis virus membrane glycoprotein and varicella virus membrane glycoprotein. FMGs and their sequences are described further in U.S. Provisional Application Ser. No. 60/193,977, filed Mar. 31, 2000, the entirety of which is incorporated by reference herein.

As discussed above, the ability to target gene expression to tumor cells is an essential prerequisite for safe and effective gene therapy of cancer. The more potent the therapeutic gene that is used (i.e., the more toxic), the greater is the need for tight control of its expression to avoid toxicity in non-cancer cells. For example, transcriptional elements which lead to 'phenotypic' tissue specificity of transgene expression with a GM-CSF therapeutic gene (Diaz, et al., J. Virol., (1998) 72: 789–795, incorporated by reference herein) are insufficient to limit the expression of a much more potent FMG cDNA to the specific cell types in which the GM-CSF gene is expressed.

Therefore, in one embodiment of the invention, an FMG encoding sequence is operably linked to a highly tumor-specific promoter which results in FMG expression greater than 100-% fold to 1000-fold in tumor cells compared to non-tumor cells. In one embodiment of the invention, the positive feedback loop described above is used to amplify the tumor specific gene expression of an FMG. In this embodiment, an amplification promoter element, such as an HSE, is cloned upstream of a highly tumor-specific promoter which in turn is cloned upstream of an FMG-encoding sequence. The tumor specific expression of FMG is validated by performing a nested polymerase chain reaction (PCR) protocol, to verify that the FMG gene is silent in all cell types except the specific tumor type corresponding to the tumor-specific promoter. In one embodiment, the expression of the FMG gene is evaluated in at least 6 different cell types (e.g., different types of normal tissues and/or different types of tumors), at least 5 of which must not express FMG.

The positive feedback loop according to the invention has three principal advantages where a gene encoding a cytotoxic protein is used as the therapeutic transgene, and HSE and HSF-1 are used as the amplification promoter element, and amplification promoter element transcription element, respectively: 1) it leads to highly tissue specific expression of a very potent cytotoxic gene; 2) it allows increasing levels of the cytotoxic gene to be expressed which leads to very effective local tumor cell killing; and 3) it also leads to the expression of HSF-1 which transactivates endogenous HSE elements and leads to cell type-specific expression of cellular stress proteins, including hsp70 and natural killer (NK) cell receptors. The induction of heat shock proteins (hsps) is a highly potent immune adjuvant to tumor cell killing and leads to the generation of long term anti-tumor immunity. See, e.g., Melted, et al., Nat Med. 4: 581–587 (1998); Todryk, et al., J Immunol 163: 1398–1408 (1999); Srivastava, et al., Immunity 8: 657–665 (1998), the entireties of which are incorporated herein by reference.

Therefore, in one embodiment, a construct is provided which comprises a stress-responsive transcriptional activator (e.g., HSF-1) encoding gene, and the expression of the FMG is responsive to a stressor (e.g., heat). However, in a further embodiment, a mutant form of the stress-responsive transcriptional activator which is constitutively active even in the absence of stress (see, Zuo, et al., Mol. Cell. Biol. 15: 4319–4330 (1995), who disclose constitutively active HSF-1 proteins) is cloned downstream of an FMG cDNA. In this embodiment, low levels of expression from the cell type-specific promoter (e.g., tissue-specific and/or tumor-specific promoter) is observed to initiate expression of both FMG and the transcription activator encoding sequences; the expression of both transgenes is amplified as the transcription activator sequences accumulate in the cell.

Delivery of Nucleic Acid Constructs to Target Tissues

Nucleic acid molecules and constructs providing therapeutic transgenes under the control of highly cell-type specific promoters and amplification promoter elements, can be incorporated into a vector and administered to any mammal, including a human. Many such vectors are commercially available, and other suitable vectors can be readily prepared and obvious to the skilled artisan. The exact design of the vector depends on such factors as the choice of the host cell to be transformed and/or the type of protein desired to be expressed. Suitable vectors can be produced by ligating the desired construct into a plasmid or viral vector suitable for expression in eukaryotic cells (see, for example, Broach, et al., Experimental Manipulation of Gene Expression, ed. M. Inouye (Academic Press, 1983) p. 83; Molecular Cloning: A Laboratory Manual, 2nd Ed., ed. Sambrook, et al. (Cold Spring Harbor Laboratory Press, 1989) Chapters 16 and 17, the entireties of which are incorporated by reference herein).

Examples of vectors that can be used include, but are not limited to, plasmids such as pBR322, pUC, or Co1E1; adenovirus; Sindbis virus; simian virus 40; *cytomegalovirus*; and retroviral vectors such as murine sarcoma virus, mouse mammary tumor virus, Moloney murine leukemia virus, and Rous sarcoma virus. Bacterial vectors can be used, such as *Salmonella* ssp., *Yersinia enterocolitica, Shigella* spp., *Vibrio cholerae, Mycobacterium* strain BCG, and *Listeria monocytogenes*. Minichromosomes such as MC and MC1, bacteriophages, cosrrids (plasmids into which phage lambda cos sites have been inserted) and replicons (genetic elements that are capable of independent extrachromosomal replication).

The vectors described above can additionally comprise sequences encoding one or more selectable markers, including, but not limited to, the gene that encodes dihydrofolate reductase and the genes that confer resistance to neomycin, tetracycline, ampicillin, chloramphenicol, kanamycin and streptomycin resistance. To improve incorporation into the genome of the target cell (if desired), a retroviral vector can be used, and long terminal repeat (LTR) sequences can be added on either side of the expression construct (see, e.g., Vile, et al., Virology 214: 307–313 (1995), the entirety of which is incorporated by reference herein).

Delivery of a therapeutic transgene under the control of a highly cell-type specific promoter can be by any means known in the art, including oral or intranasal administration; intramuscular, intradermal, intraperitoneal, or subcutaneous injection, including injection using a biological ballistic gun ("gene gun"). Administration of the therapeutic transgene can be repeated at any desired interval as needed to achieve therapeutic efficacy. Additional components can be added to a vector to improve its selective delivery to target cells and to repress its delivery to non-target cells. Examples of approaches that can be used include host range extension, entry enhancement, and host range restriction, as described in Peng and Russell, Cur. Opin. Biotech. 10: 454–457 (1999), the entirety of which is incorporated herein by reference.

The above disclosure generally describes the present invention. A more complete understanding can be obtained by reference to the following specific examples, which are provided herein for purposes of illustration only and are not intended to limit the scope of the invention.

EXAMPLES

Plasmids and Cell Lines

For the analysis of melanoma specific gene expression, plasmids and viruses were transduced into either melanoma (MeWo, Me1624, A378M, B16 or 1735) or non-melanoma (HT1080; 293; Vero, Tel.CeB6, HeLa, CMT93) cell lines. The human tyrosinase promoter plasmids (300 base pairs; 115 base pairs or 65 base pairs) are as described by Bentley et al., supra, and Diaz, et al., supra. The TDE-SVO plasmid consists of three repeated copies of the base pairs Tyrosinase Distal Element (TDE) upstream of the minimal SV40 basal promoter (Promega) (Diaz, et al. J. Virol. (1998) 72:789–795, the entirety of which is incorporated by reference herein). The cDNA of the mutated HSF-1 transcription factor is described in Zuo, et al., Mol. Cell Biol. 15:4319–4330, (1995) (the entirety of which is incorporated by reference herein) and consists of a deletion of the wild type HSF-1 cDNA corresponding to amino acid positions 202–316. The HSE element-5'-AGAATGTTCTAGAAG-3' (SE0 ID NO:2) was synthesized as a consensus sequence which confers heat shock and HSF-1 responsiveness on heterologous genes as described in Amin, et al., Mol. Cell Biol. 8:3761–3769 (1988) and Goldenberg, et al., J. Biol. Chem. 263:19734–19739 (1988), the entireties of which are incorporated by reference herein.

To assess promoter/enhancer strengths, plasmids were constructed using standard techniques such that different promoters and promoter/enhancer fragments were placed upstream either of the Chloramphenicol Acetyl Transferase (CAT) gene (Diaz, et al, supra), the human GM-CSF gene (Wong, et al., Science 228: 810–815 (1985), the entirety of which is incorporated by reference herein) or the cDNA of the Gibbon Ape Leukaemia Virus fusogenic membrane glycoprotein (GALV-FMG) (Bateman, et al. Cancer Res. 60: 1492–1497 (2000); Fielding, et al., supra, the entireties of which are incorporated by reference herein). Levels of gene expression were assayed using either CAT assays (Diaz, et al., supra), by measuring levels of human GM-CSF secreted from the plasmids by ELISA (Pharmingen) or by semi-quantitative RT-PCR as described below.

Hybrid LTR retroviral vectors were constructed from the parental Mo-MLV retroviral plasmid pBabePuro (Morgenstern, et al., Nucleic Acids Research 18: 3587–3596 (1990), the entirety of which is incorporated herein). Manipulations to the 3'LTR were made in the plasmid pSKLTR followed by reassembly into the pBabePuro plasmid through Clal-Pvul ligations as described in Diaz, et al., supra.

Analysis of Gene Expression from Cells by Reverse Transcriptase Polymerase Chain Reaction RNA was prepared from cultured cell lines with the RNA Easy® kit (Qiagen) according to the manufacturer's instructions. RNA concentrations were measured and 1 $\mu$g total cellular RNA was reverse transcribed in a 20 $\mu$l volume using oligo-(dT) as a primer and Moloney murine leukaemia virus reverse transcriptase (Pharmacia LKB Biotechnology, Milton Keynes, (U.K.). A cDNA equivalent of 1 ng RNA was amplified by the polymerase chain reaction using primers specific for the target genes. PCR was performed in a 50 $\mu$l reaction mixture with 250$\mu$M of each dNTP, 100 nM of primers, 5 $\mu$l of 10x buffer (HT Biotechnology Ltd, Cambridge, U.K.), and 1 unit of super Taq DNA polymerase (HT Biotechnology Ltd, Cambridge, U.K.), using 30 cycles. The reaction mix (25 $\mu$l samples) was analyzed by agarose get electrophoresis (1%) in TAE buffer containing 0.2 $\mu$g/ml ethidium bromide. In all experiments, a mock PCR (without added DNA) was performed to exclude contamination. To exclude carry over of genomic DNA during the RNA preparation step, controls were also carried out in which the reverse transcriptase enzyme was omitted.

Cell Transfection and FMG-mediated Cell Killing Assays

To assess the cytotoxicity of the GALV FMG driven by the HSE-Tyr-300, Tyr-300 or the CMV promoters, cells were plated in 6 well plates at a density of $5 \times 10^5$ cells per well. 24 hours later, each well was transfected with 5 $\mu$g of the appropriate plasmid DNA using calcium phosphate transfection (Profection®, Promega, Wis.) according to the manufacturer's instructions. 4 hours later the cells were washed three times in serum free medium and then incubated in normal, serum containing medium for a further 72 hours. Plates were either counted for living cells to assess the levels of cell survival (as described in Bateman, et al., supra) or were stained with Crystal violet to obtain a qualitative, pictorial representation, of the degree of cytotoxicity. To determine the heat shock sensitivity of the HSE element, the appropriate plates were sublethally heat shocked at 42° C. for 30 minutes.

Generation of Retroviral Vector Stocks

The GALV FMG cDNA was subcloned into the pBabePuro vector backbone at the EcOR1 sites in the polylinker using standard techniques. Subsequently, the cDNA for the HSF-ld202-316 transcription factor (Zuo, et al., supra) was subcloned downstream of the GALV cDNA into the Sal1 site of the pBabePuro polylinker leaving a 24 base pair linker to separate the GALV and HSF-1d202–316 genes. This C-type vector was packaged into viral particles by transfection of 5 $\mu$g of plasmid DNA into the 293INT cell line which stably expresses the MoMLV gag and pol genes but no envelope along with 5 $\mu$g of the plasmid pMD.G encoding the VSV-G envelope protein (see, Naldini, et al., Science 272: 263–266 (1996); Zufferey, et al., Nat Biotechnol. 15: 871–875 (1997), the entireties of which are incorporated by reference herein).

Transfections were carried out in a 10 cm plate out using the Profection (calcium phosphate co-precipitation) method (Promega, Wis.). 48–72 hours following transfection, cell supernatants were recovered, filtered through a 0.45 $\mu$m filter and either used directly for infection or frozen at –80° C.

Viral infections were performed by exposing exponentially growing target cells, (either melanoma, Me1624 or MeWo) or non-melanoma (HT1080, 293 or TelCeB6), to different dilutions of viral supernatants in serum free medium for 4 hours in 24 well plates. The infectious medium was then removed and cells were washed three times before being allowed to grow in normal growth medium for a further 120 hours. At this stage, infected cultures were counted for living cells to assess the levels of cell survival.

Example 1

Identification of a Highly Melanoma Specific 300 Hi, Element of a Human Tyrosinase Promoter The specificity of enhancer+promoter elements for expression of a CAT reporter gene was compared in human melanoma cell lines (B 16, A378M) and human non-melanoma cell lines (HT1O8O, 293, Tel.CeB6). Plasmid construction and transfection were as described in Diaz et al., supra. Reverse transcriptase PCR was performed as described in Vile et al., supra.

Figure 2:
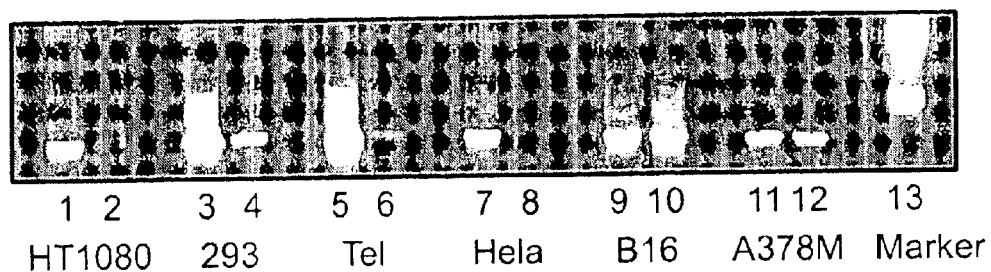
FIG. 2 shows the results of RT-PCR to detect expression from CMV promoters (odd numbered lanes) or TDE-SV40 (even numbered lanes; SV40: Simian Virus 40) in non-melanoma cells (HT1080, 293, Tel.CeB6 or Hela cells, as indicated) and melanoma cells (B16 or A378M). Equal loading was verified with a GAPDH control (not shown).

The results of RT-PCR analysis are shown in FIG. 2. The TDE-SV40 element is clearly preferentially active in melanoma cells, but this specificity is not sufficient to prevent a highly potent gene such as GALV from being toxic in non-melanoma cells.

Figure 3A:
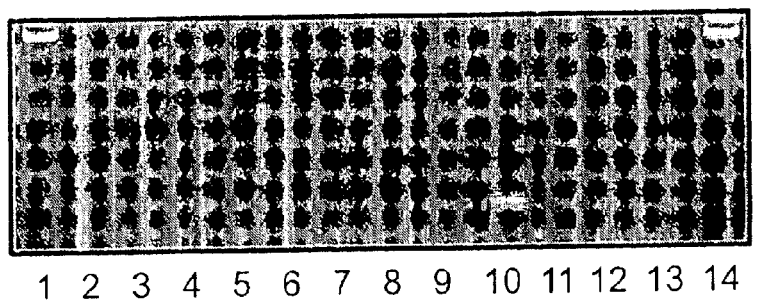
FIGS. 3A and 3B illustrate the high selectivity of a human tyrosinase 300 base pair (base pair) promoter element using nested RT-PCR assay.
Figure 3B:
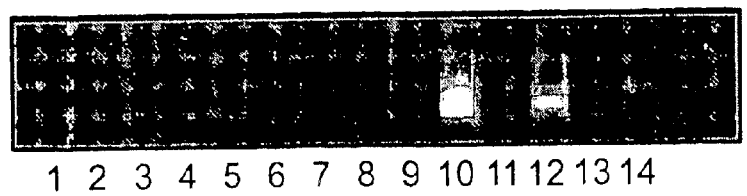

Different lengths of the basal promoter from the human tyrosinase gene were surveyed in search of a promoter which is genuinely transcriptionally silent in non-melanoma cells. Using a sensitive nested RT-PCR assay with chloramphenicol acetyltransferase (CAT) as the reporter gene (the primers used were 5'-ATGGAGAAAAATCACTGGA-3 (SEQ ID NO:3) and 5'-GAGACGAAAAACATATTCTCA-3' (SEQ ID NO:4)), a 115 base pair element that was previously reported to be melanoma-pecific (Bentley, et al., supra) was found to possess transcriptional activity in some of the non-melanoma cells tested (FIG. 3A). However, a 300 base pair element (Tyr300) was transcriptionally silent in all of the non-melanoma cell lines tested, yet retained activity in human and murine melanoma cells (FIG. 3B).

Example 2

HSE Adds Inducibility by Heat Shock Proteins to a Tyr300-SV40 Promoter

A consensus HSE sequence (5'-AGAATGTrCTAGAAG-3', SEQ ID NO:2) was synthesized and incorporated upstream of the melanoma-specific Tyr300 promoter element controlling a reporter gene encoding GC-CSF. This HSE consensus sequence confers heat shock inducibility on reporter genes (Zuo et al, supra; Goldenberg et al., J. Biol. Chem. 263: 19734–39 (1988)). Two plasmids were made in which HSE was separated from the Tyr300 promoter by either one full turn (10 nucleotide bases) of the DNA helix (HSE-Tyr300-FULL-GM-CSF) or by one-half turn of the helix (HSE-Tyr300-HALF-GM-CSF).

Transient transfection of a human non-melanoma line (HT 1080) with 20 ug of either a Tyr-300-GM-CSF plasmid, an HSE-Tyr 300-FULL-GM-CSF plasmid, or an HSE-Tyr 300-HALF-GM-CSF plasmid generated no detectable GM-CSF product 72 hrs following transfection (data not shown). Co-transfection of these same cells with HSF-1 cDNA also failed to produce any GM-CSF production (see FIG. 4, condition 1). Human melanoma cells (MeWo cell line) transfected with 20 ug of either the Tyr 300-GM-CSF (FIG. 4, condition 2) or the HSE-Tyr 300-FULL-GM-CSF plasmid (FIG. 4, condition 6) express only very low amounts of GM-CSF, similar results were obtained with the HSE-Tyr 300-HALF-GM-CSF plasmid (not shown).

Figure 4:
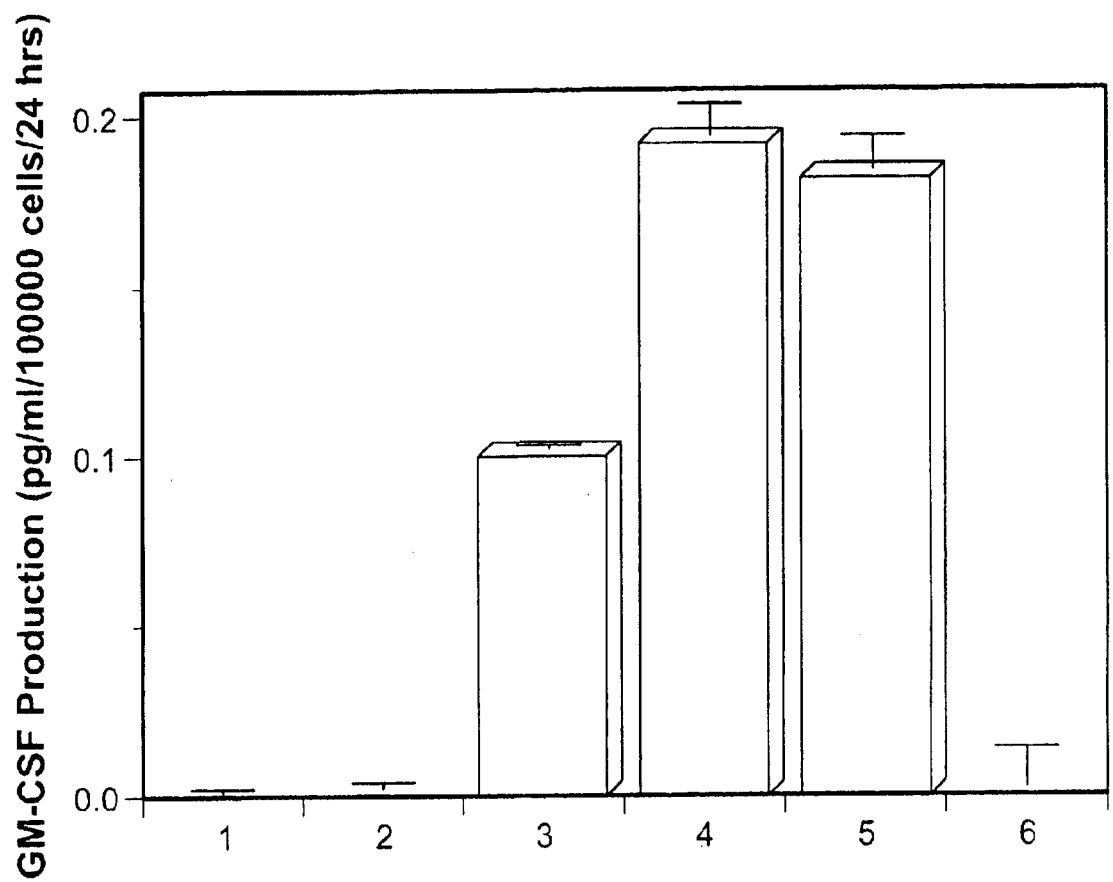
FIG. 4 demonstrates that HSE confers heat-shock and mHSF-1 inducibility on the melanoma-specific Tyr 300 base pair promoter. MeWo cells transfected with the Tyr 300-GM-CSF (condition 2) or the HSE-Tyr300-FULL-GM-CSF plasmids (condition 6) express only very low amounts of GM-CSF, demonstrating that Tyr 300 is a very weak promoter. However, transfection of the human melanoma MeWo line with the TDE-SV40-GM-CSF plasmid (condition 3) leads to easily detectable levels of GM-CSF production. In the presence of either heat shock (e.g., 42° C., 30 minutes, condition 4) or a co-transfected InHSF-1 plasmid (condition 5), GM-CSF production is increased significantly following transfection with the HSE-Tyr300-GM-CSF plasmid. Co-transfection of a non-melanoma cell line (HT1080) with the HSE-Tyr 300-GM-CSF plasmid and the HSF-1 cDNA did not yield any detectable GM-CSF production (condition 1).

This demonstrates that Tyr 300 is a very weak promoter. However, transfection of MeWo cells with 20 µg of the TDE-SV40-GM-CSF plasmid (FIG. 4, condition 3) leads to easily detectable levels of GM-CSF production (see also Diaz et al., J. Virol. (1998) 72:789–95). In the presence of either heat shock (42° C., 30 minutes; FIG. 4, condition 4) or co-transfection with 20 µl of mHSF-1 plasmid (FIG. 4, condition 5), GM-CSF production is increased significantly following transfection with the HSE-Tyr 300-FULL-GM-CSF plasmid and increased to a lesser degree using the HSE-Tyr300-HALF-GM-CSF plasmid (not shown). These experiments demonstrate that the HSE-Tyr300 base pair promoter is both tissue-specific and can be induced by mHSF-1.

Example 3

Induction Of Bsp70 using HSE and Constitutively Active Mutant HSF-L.

Figure 5:
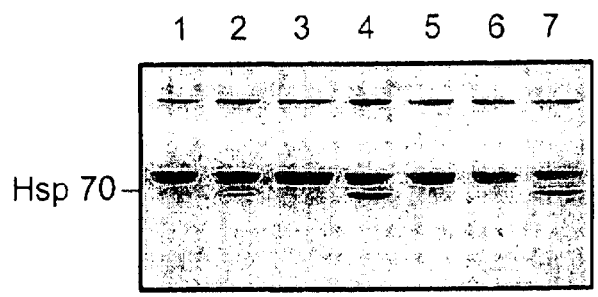
FIG. 5 demonstrates hsp70 expression following transient transfection of murine melanoma cells with mutant HSF-1. An immunoblot is shown for Hsp70 expression in B16 cells stably expressing constitutively active human mHSF-1 (deletion 202–316). Lysates of untransfected B-16 cells are shown in lane 1. Lane 2 shows the pooled population of HSF-1 transfected colonies. Lanes 3–7 show clones of individual HSF-1 transfected colonies.

Hsp70 expression was probed by Western blotting using antibody BRM-22 (Sigina Chemical Co., St. Louis, Mo.) in B16 cells stably expressing constitutively active human mHSF-1 (deletion 202-3 16). The resulting immunoblot is shown in FIG. 5. Lysates of untransfected B-16 cells are shown in lane 1. Lane 2 shows the pooled population of HSF-1 transfected colonies. Lanes 3–7 show clones of individual HSF-1 transfected colonies. Mock transfected cells or cells transfected with irrelevant plasmnids did not show induction of hsp70. Expression of hsp70 correlated exactly with expression of MHSF-1 assayed by Western Blotting of the pools and clones (data not shown).

Example 4

Figure 7A:
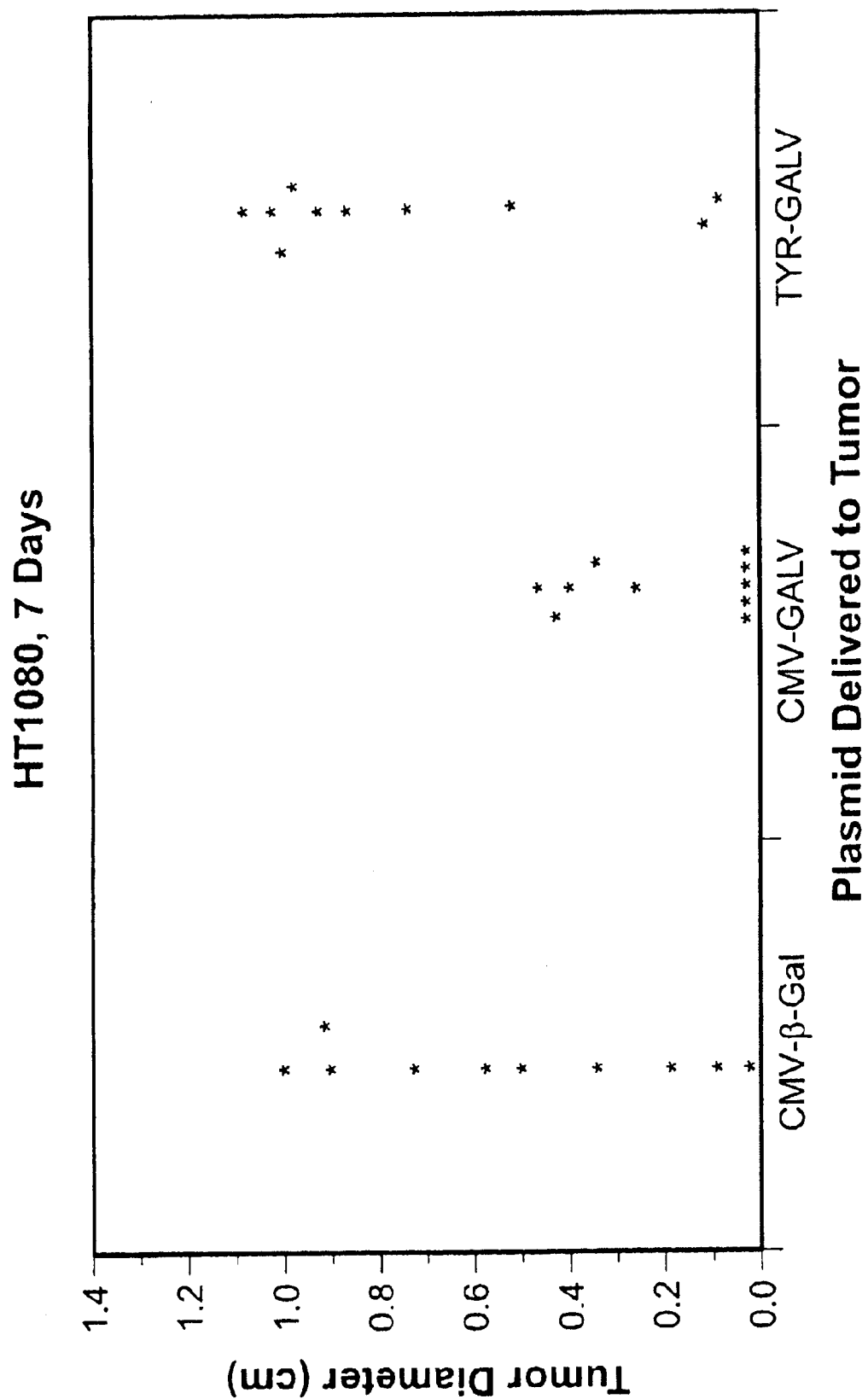
FIGS. 7A–7D demonstrate the elimination of primary tumors by plasmids containing cell type-specific promoter elements. See Example 4 for details.
Figure 7B:
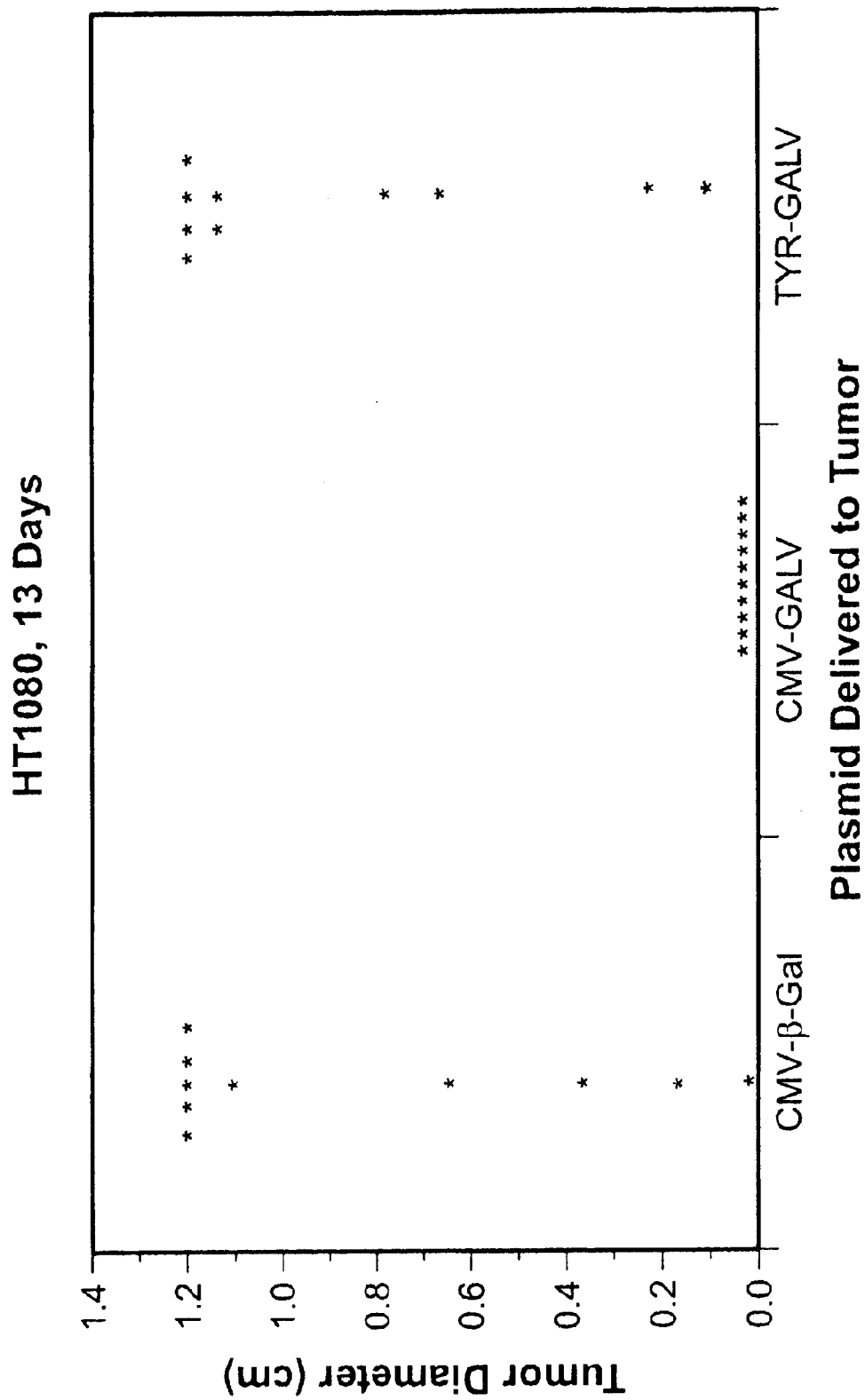

Selective Elimination of Human Melanoma Tumor Growth using a Tyr300-GALV Construct HT1080 (human fibrosarcoma) or Me1624 (human melanoma) tumors were seeded subcutaneously in nude mice ($10^6$ cells per mouse). Growing tumor cells were transduced in situ with 10 ug/tumor of CMV-δ-Gal, CMV-GALV or Tyr300-GALV plasmid DNA complexed with Efectene lipid (Qiagen). The CMV β-Gal plasmid was constructed by cloning β-galactosidase cDNA into the EcOR1 site of the plasmid pCR3 (Invitrogen) with expression driven by the CMV promoter. The CMV-GALV plasmid was constructed by cloning GALV cDNA into the EcOR1 site of pCR3 with expression driven by the CMV promoter. The Tyr300-GALV plasmid was constructed by cloning the HSE-Tyr300 element upstream of the GALV cDNA into the EcOR1 site of pCR3; for this condition the cells were cotransfected with MHSF-1 in pCR3. Ten mice were injected per group. At seven days following DNA injection of HT1080 tumors, those injected with CMV-GALV plasmid began to regress compared with the progression of tumors in the other two groups (FIG. 7A). In the same mice at 13 days after transduction, tumor size in some groups reached 1.2 cm in the longest diameter, at which point those animals were sacrificed. The tumors in the CMV-GALV-injected group had all regressed and had been eliminated (FIG. 7B). Animals in which tumor size had not reached 1.2 cm by day 13 were maintained and tumor size was followed.

Figure 7C:
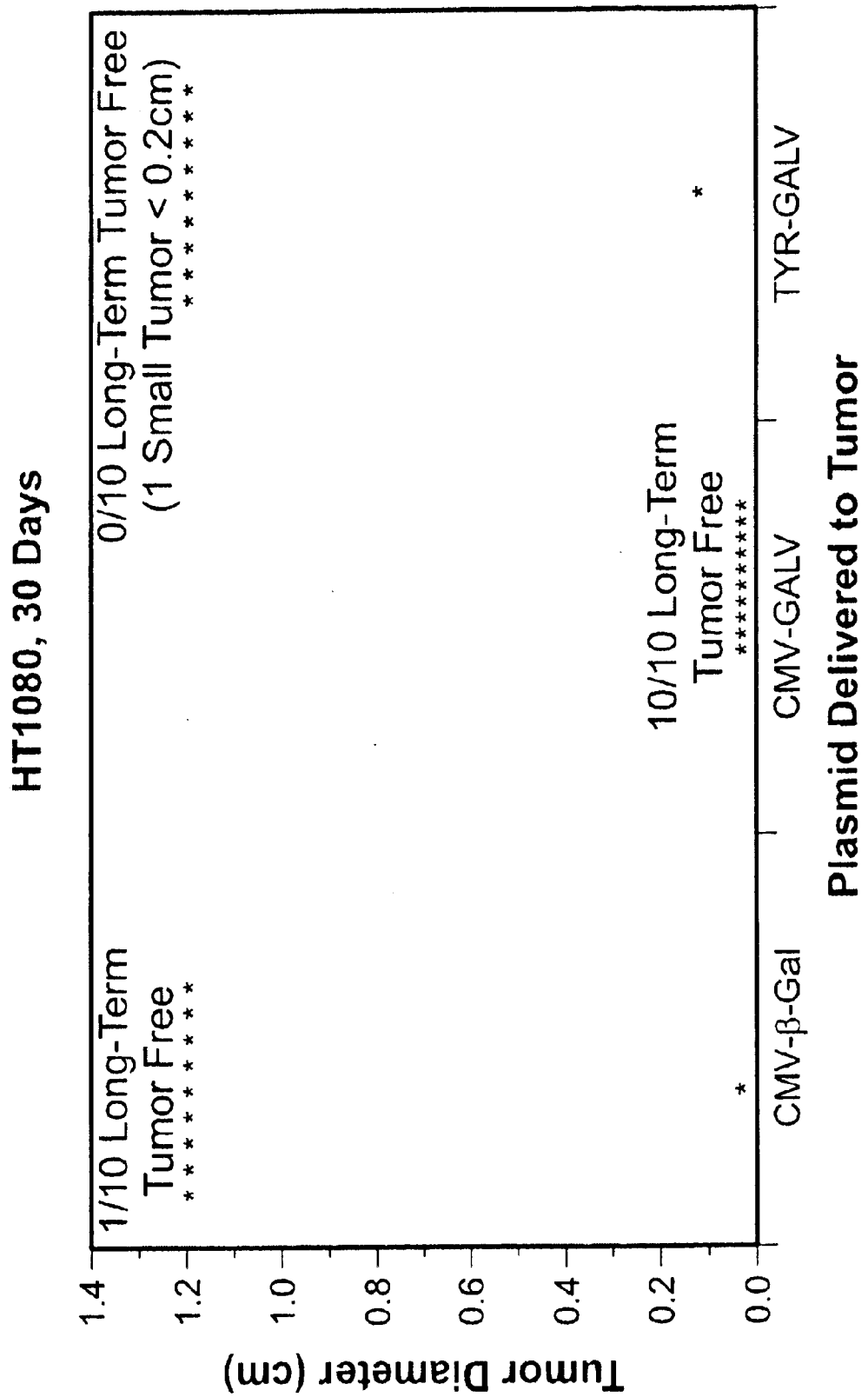
Figure 7D:
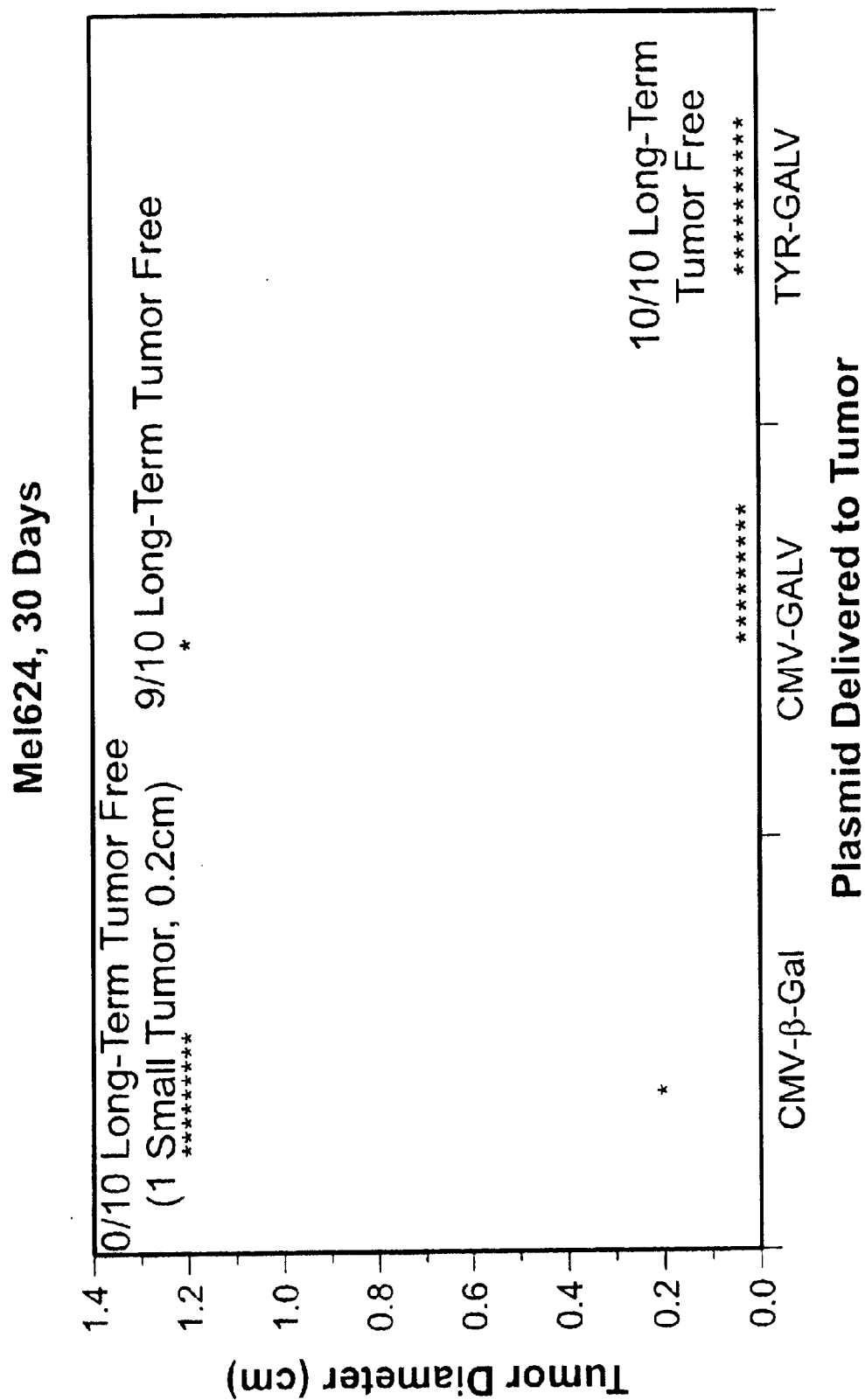

By day 30 following transduction of tumors, nearly all mice in the CMV-β-Gal and TYR-GALV groups had eventually developed tumors which reached 1.2 cm in diameter and were sacrificed (FIG. 7C). Long term tumor-free mice (shown over each group) were scored as those having no detectable tumor by the end of the experiment. Progression of transduced human melanoma tumors, Me1624, was similar to that shown for the HT1080 tumors. By the end of the experiment (day 30 after transduction), 90% the tumors transduced with the CMV-GALV plasmid had been eliminated. The one tumor recurrence in this group developed 23 days following DNA delivery. In contrast, 100% of the tumors transduced with the TYR-GALV plasmids were eliminated and no regrowths were observed.

Example 5

The Efficacy of Transcriptional Targeting Depends on the Potency of the Transgene Being Expressed In one embodiment, the cDNA of the GALV FMG protein was cloned downstream of the TDE-SV4O element to induce melanoma-specific cell killing in vitro. Transfection of the TDE-SV4O-GALV plasmid into three different human melanoma cell lines induced large amounts of cell fusion 24–48 hours following transfection, at levels comparable to that produced by a CMV-GALV construct. When transfected into 5 human non-melanoma cell lines, the TDE-SV4O-GALV construct showed a clear lag period in the formation of syncytia compared to CMV-GALV. However, in the majority of the lines, significant amounts of cell fusion subsequently developed after 72–96 hours as shown in Table 1, below.

| Cell Line | CMV GALV | TDESV40 GALV |
|---|---|---|
| Syncytium Formation 24 hrs Post Transfection | | |
| HT1080 | +++ | +/− |
| 293 | +++ | + |
| Tel | +++ | +/− |
| Vero | +++ | − |
| MeWo | +++ | +++ |
| A378M | +++ | +++ |
| Syncytium Formation 96 Hours Post Transfection | | |
| HT1080 | +++ | ++ |
| 293 | +++ | +++ |
| Tel | +++ | ++ |
| Vero | +++ | + |
| MeWo | +++ | +++ |
| A378M | +++ | +++ |

+++: 70–100% of all the cellls on the plate have been recruited into syncytia;
++: 30–70% of cells are within syncytia;
+: between 10 and 30% are within syncytia; and
+/−: means that fewer than 10% of cells are within syncytia.

Figure 8:
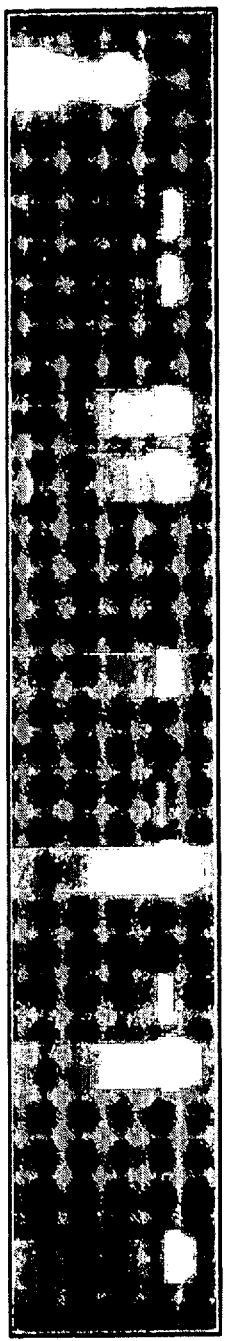
FIG. 8 shows the results of RT-PCR experiments to determine expression of a transgene (GALV) from the CMV (odd numbered lanes) or TDE-SV40 (even numbered lanes) promoters in non-melanoma (HT1080, 293, Tel.CeB6 or Hela cells, lanes 1–8) and melanoma cells (B16 and A378M, lanes 9–12). Equal loading was verified with a GAPDH control (data not shown).

To confirm that expression from the TDE-SV4O enhancer/promoter is genuinely melanoma-preferential, a semi-quantitative RT-PCR assay was used (FIG. 8). Levels of transcripts from the TDE-SV4O promoter were significantly lower than those from the CMV driven construct in all non-melanoma cell lines, but were close to equivalent in the melanoma cell lines (FIG. 8). Thus, the melanoma cell specificity of TDE-SV40 is real but is not sufficient to prevent a highly potent gene such as GALV from being toxic in a proportion of non-melanoma cells.

Example 6

Figure 9A:
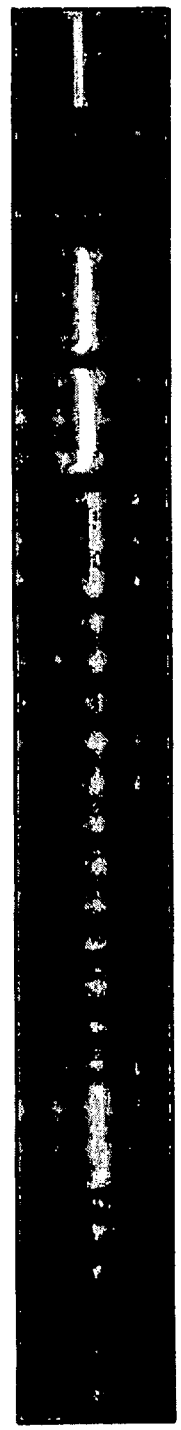
FIGS. 9A–B illustrate that different elements of the Tyr promoter have different levels of expression in non-melanoma cells.
Figure 9B:
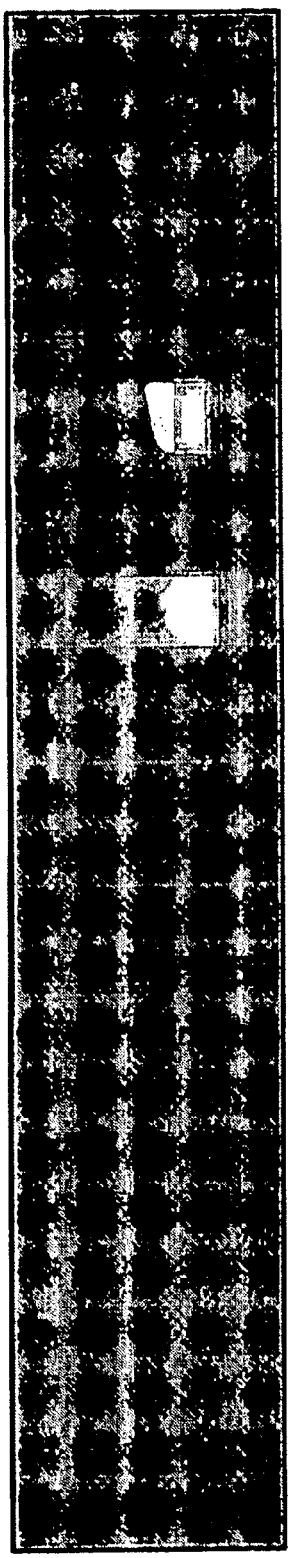

Identification of an Element of the Human Tyrosinase Promoter that is Transcriptionally Silent in Non-Melanoma Cells But Retains Activity in Melanoma Cell Lines In one embodiment, fragments which ranged from +80 to −65, −115 or −300 from this basal Tyr promoter were evaluated using both CAT expression and RT-PCR assays to screen for expression. Both the 65 base pair and the 115 base pair fragments of the promoter showed some transcriptional activity by RT-PCR in some, or all, of the non-melanoma cells tested (FIG. 9A). In contrast, using a sensitive nested RT-PCR assay, the 300 base pair element of the tyrosinase promoter was transcriptionally silent in all of the non-melanoma cells tested but retained activity in the human and murine melanoma cells (FIG. 9B). However, when the CAT, GM-CSF, or GALV genes were cloned downstream of the 300 base pair promoter, levels of transgene expression were low, and melanoma cells transfected with the Tyr 300-GALV construct showed limited cell cytotoxicity at only about 10% of the levels produced by CMV-GALV (FIG. 14).

Example 7

Amplification of Low Level Expression from a Weak, but Tissue-Specific, Promoter using a Second Transcriptional Regulatory Element Since levels of expression from highly cell type-specific promoters are generally not therapeutic, even when highly potent genes (e.g., cytotoxic) genes such as FMGs are used, in one embodiment, an amplification promoter element was operably linked to an FMG under the control of a highly cell type-specific promoter. In one embodiment, an amplification promoter comprising a consensus HSE sequence (5'-AGAATGTTCTAGAAG-3': SEQ ID NO:2) modified from the construct described in Goldenberg, et al., supra, and Todyry, et al., supra, was synthesized.

Figure 10A:
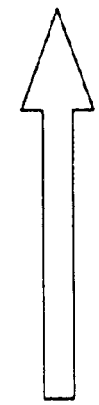
FIGS. 10A and 10B illustrate that the HSE element confers heat-shock, and HSF-1d202–316, inducibility on the melanoma-specific Tyr 300 base pair promoter.
Figure 10B:
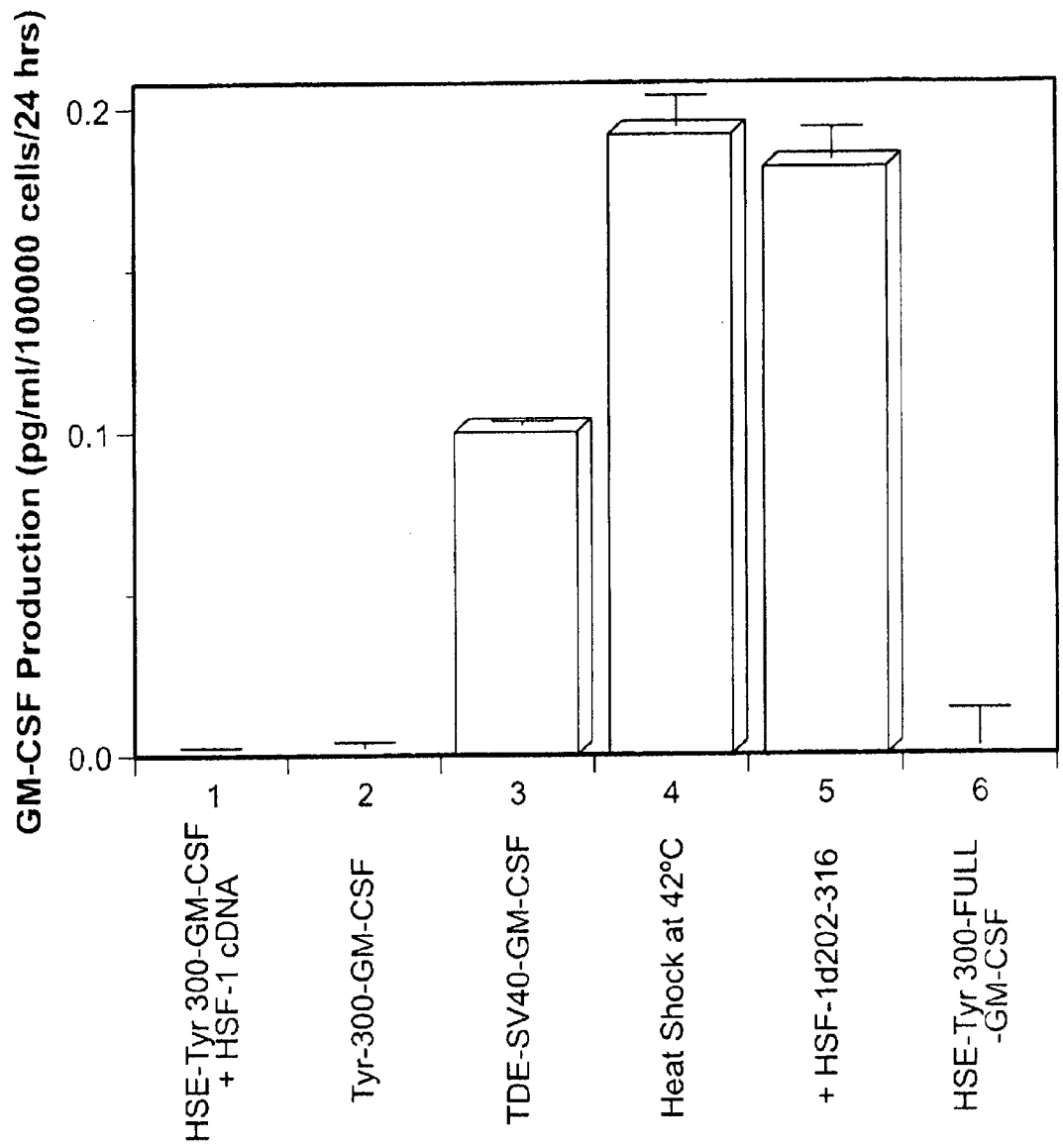

In order to investigate whether it was necessary to optimize the topological spacing of the HSE element relative to any of the 5 characterized important DNA/protein binding sites within the 300 base pair element of the tyrosinase promoter, plasmids were made in which the HSE element was separated from the C nucleotide at position-300 of the Tyr-300 promoter by either no nucleotides or one full turn of the DNA helix (HSE-Tyr 300-FULL) or by a stuffer fragment representing one half turn of the helix (HSE Tyr-300-HALF) (FIG. 10A). Both HSE-Tyr 300-GM-CSF plasmids transfected into MeWo melanoma cells produced the same low levels of GM-CSF as the Tyr300-GM-CSF plasmid (FIG. 10B). However, when the transfected cells were heat shocked 42° C. for 30 minutes, 24 hours following transfection, GM-CSF production was increased, but only in cells transfected with the HSE-Tyr300 plasmids (FIG. 10B).

Several experiments demonstrated up to a three fold increase in GM-CSF production from melanoma cells transfected with the HSE-Tyr 300-FULL construct compared to the HSE-Tyr 300-HALF construct (data not shown). The non-melanoma line HT 1080, similarly treated, did not produce any GM-CSF either with or without heat shock in vitro (data not shown). Similar results were obtained from RT-PCR studies performed on melanoma and non-melanoma cells transfected with the HSE-Tyr 300-FULL or HSE-Tyr 300-HALF constructs, confirming both the tissue specificity of GM-CSF expression from melanoma cells, as well as the increased level of message using the HSE-Tyr 300-FULL construct (data not shown). Hfence, the HSE element cooperates with the Tyr300 base pair promoter to induce tissue-specific expression, an effect which can be optimized by engineering the topology of the spacing of the two separate elements.

Example 8

Transcriptional Transactivation of the HSE-Tyr300 Base Pair Tissue-Specific Promoter is Possible using Mutant HSF-1

When the HSE-Tyr-300-FULL element was used to express the GALV FMG, transfection was unable to eradicate melanoma cells in vitro to the same extent as the CMV promoter (FIG. 14). Therefore, in one embodiment, constitutively active forms of HSF-1 were used to increase levels of expression from the tissue specific HSE-Tyr300-FULL element.

A deleted, mutant form of HSF-1, HSF-1 d202–316, was used in which deletion of amino acids 202–316 removes the sensitivity to stress dependent activation and nuclear translocation. The protein is constitutively active in the absence of cellular stress while retaining the DNA and protein binding domains required to transactivate gene expression through HSE. Co-expression of HSF-1-1d202–3 16 was demonstrated to transactivate the very weak, but highly specific, HSE-Tyr 300 promoter (FIG. 10). When HSF 1d202–316 was co-transfected into MeWo melanoma cells along with the Tyr 300-GM-CSF construct, no GM-CSF production could be detected. However, when HSF-1d202–316 was co-transfected with the HSE-Tyr 300-FULL-GM-CSF construct, levels of GM-CSF were increased significantly to a level similar to that produced by heat shock (FIG. 9B). Importantly, cotransfection of HSE-Tyr-300-GM-CSF with HSF-1d202–316 into non-melanoma cells still gave no detectable GM-CSF production (FIG. 9B). Therefore, even low levels of HSF-1d202–316 (as provided in a transient co-transfection assay) were capable of transactivating the HSE-Tyr300 base pair promoter element while retaining the tissue specificity of the tyrosinase promoter.

Example 9

Figure 11:
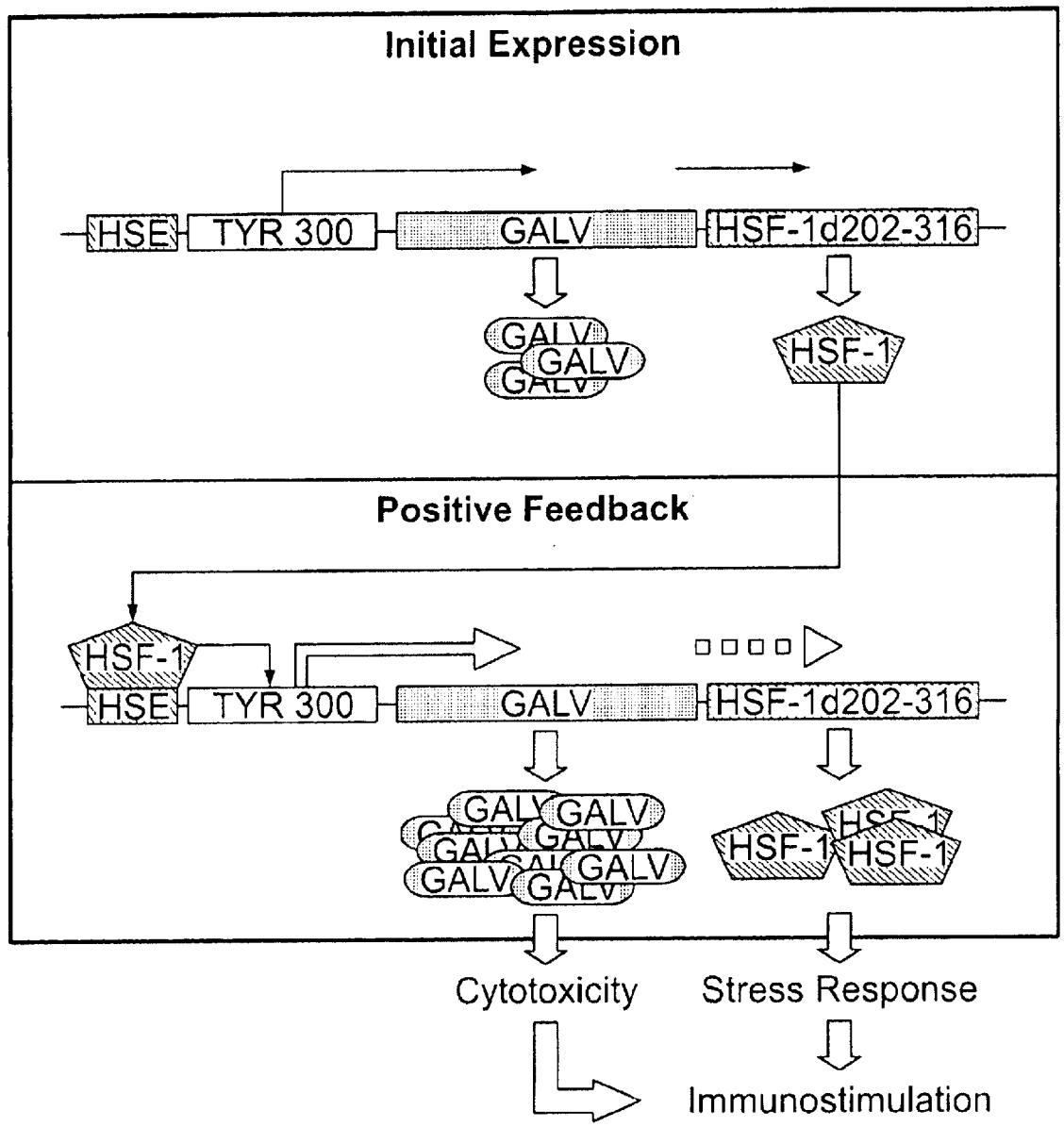
FIG. 11 shows a schematic diagram of a positive feedback loop according to one embodiment of the invention.

The HSE Transcriptional Control Element can be used to Transactivate Gene Expression from the Melanoma-Specific Tyr-300 Promoter In one embodiment, the HSE-Tyr 300 transcriptional regulatory element was used in tandem with the HSF-1d202–316 transcription factor, to regulate highly tissue-specific expression even of a very potent cytotoxic genes (FIG. 11) and to provide an immunostimulatory effect.

Figure 12:
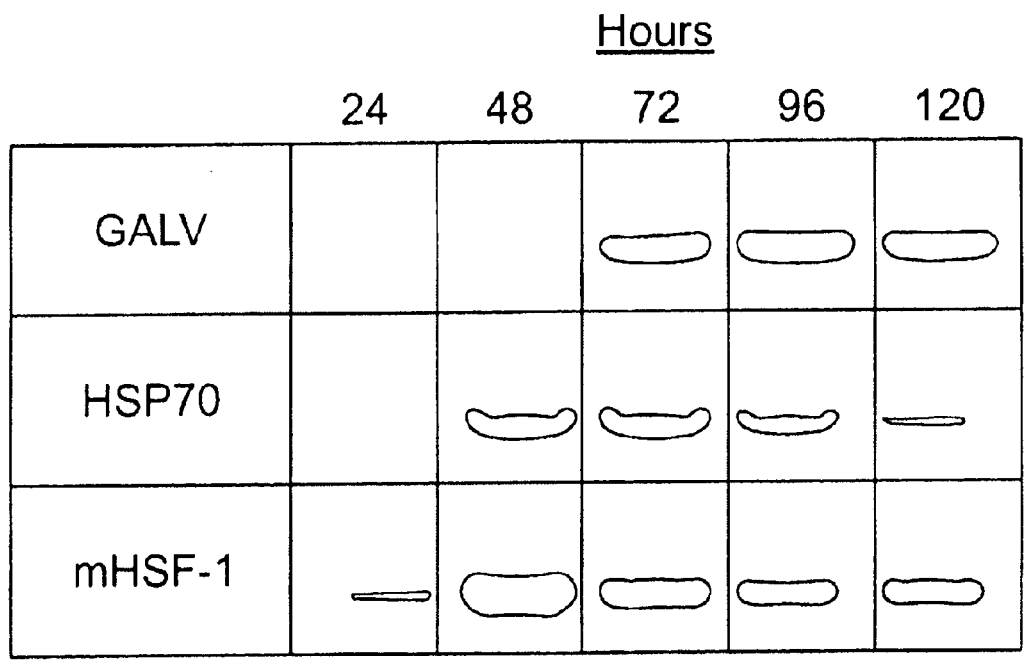
FIG. 12 shows that the transcriptional feedback loop according to the invention is operative at the transcriptional level. In one embodiment, $5 \times 10^5$ murine B16 cells, which are not fused by expression of the GALV FMG, were cotransfected with HSE-Tyr-300-GALV (5 $\mu$g) and mHSF-1(5 $\mu$g). Cells were harvested at time points following transfection as shown and RT-PCR was used to examine levels of expression of the GALV or HSF-1d202–316 transgenes and of endogenous murine hsp70.

In one embodiment, murine B 16 cells were co-transfected with HSE-Tyr-300-GALV and HSF-ld202–316 plasmids. Importantly, B16 cells are not fused by expression of the GALV FMG because they lack the Pit-1 receptor. RT-PCR was used to follow expression of the transgenes (FIG. 12). The co-transfected HSF-1d202–316 was expressed within 24 hours of transfection. However, the GALV transgene expressed from the HSE-Tyr element was not detected in appreciable amounts until 72 hrs following transfection (FIG. 12), presumably because sufficient levels of HSF-1d202–316 were required to build up in order to transactivate the HSE element. In addition, following appearance of mRNA for the transfected HSF-1d202–316, transactivation of endogenous hsp70 was detected 24 hrs later. These data confirm both the operation of the feedback loop at the transcriptional level and the induction of endogenous heat shock and stress response genes. The latter induction provides effective adjuvant functions for immunostimulation.

Example 10

Figure 13A:
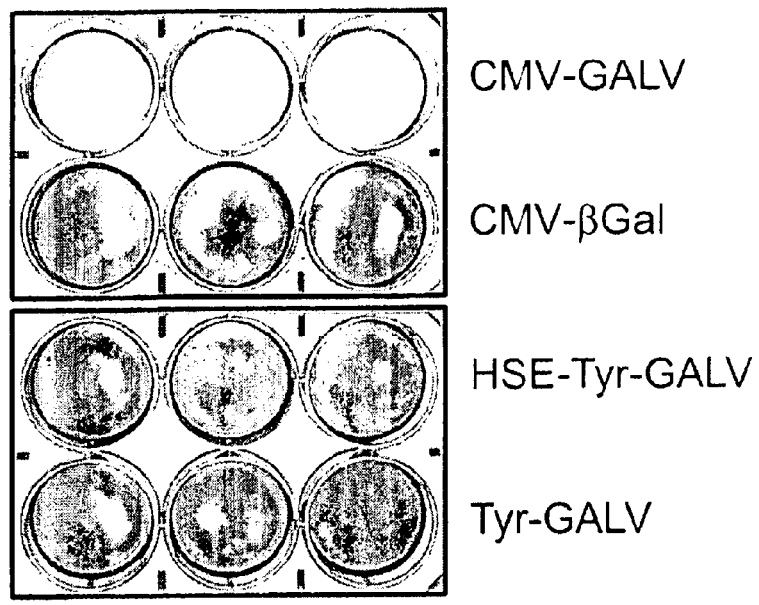
FIGS. 13A–F illustrate that the HSE-Tyr-300/HSF-1 feedback loop can be used to kill melanoma cells specifically and efficiently.
Figure 13B:
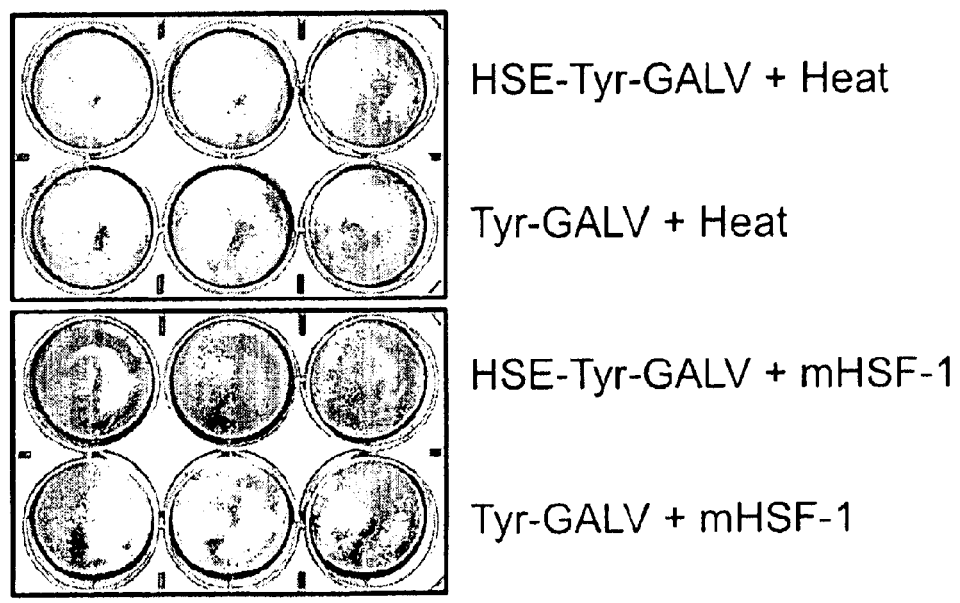

The USE-Tyr-3001/SF-1 Feedback Loop can be used to Kill Melanoma Cells Specifically-and-Efficiently To test the efficacy of the transcriptional feedback loop in vitro, the HSE-Tyr300 GALV construct was transfected into non-melanoma human cells, Tel.CeB6 (FIGS. 13A and B) or HT1080 (data not shown). The only significant toxicity was seen in the cells transfected with the CMV-GALV construct (FIG. 13A). In contrast, both the HSE-Tyr-300 and Tyr-300-GALV constructs gave low levels of toxicity when transfected into a melanoma line, Me1624 (FIGS. 13C, 13D) or similarly the MeWo line (data not shown). Quantitation of cell survival showed that the HSE-Tyr-300 construct gave small but significantly enhanced killing of MeI624 cells with respect to the Tyr-300 construct, presumably due to the proposed activation of the HSE-Tyr-300 element through induction of endogenous HSF-1 through GALV-mediated cell killing.

Figure 13C:
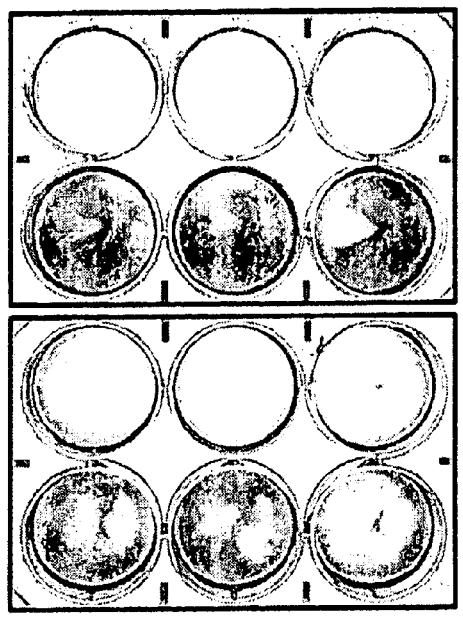
Figure 13D:
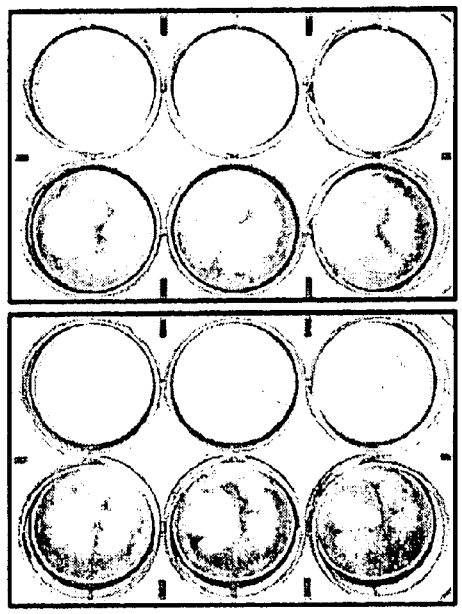
Figure 13E:
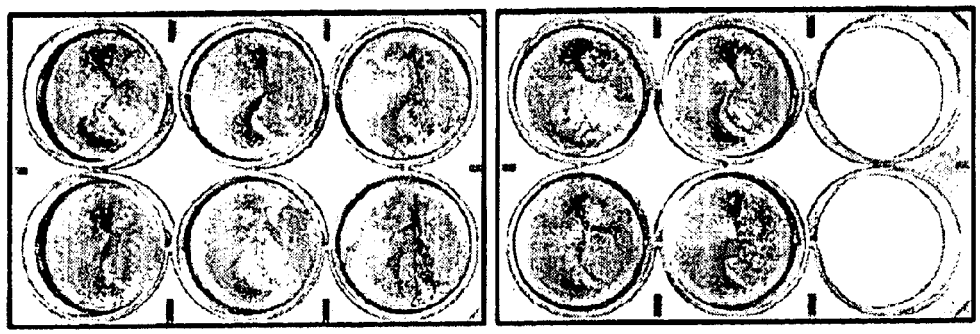
Figure 13F:
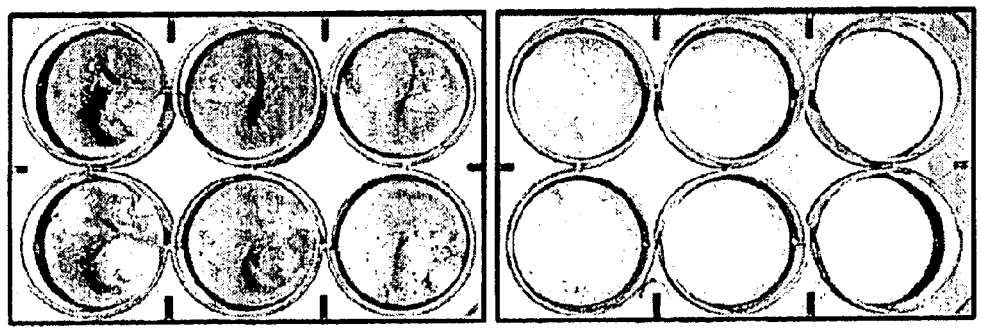

However, greatly enhanced toxicity was observed with transfection of the HSE-Tyr-300-GALV constructs when the cells were either heat shocked or co-transfected with HSF-1d202–316 (FIG. 13C, D). That the latter effects were operative through HSF-1d202–316 regulation were confirmed by the demonstration that increasing amounts of co-transfected HSF-1d202–316 led to proportional increases in killing of melanoma cells, whereas no killing was observed with increasing concentrations of an irrelevant co-transfected β-Gal plasmid (FIGS. 13E, F). Taken together, these data show that it is possible to control highly tissue-specific expression of GALV FMG either through the application of heat itself, enabling locoregional control of gene expression (see, e.g., Blackburn, et al., Cancer Res. 58: 1358–1362, (1998), the entirety of which is incorporated by reference), or through co-expression of the HSF-1d202–316 transcription factor.

Example 11

Expression of HSF-1d202–316 Induces Hsp70 and other Stress Related Proteins

As well as leading to direct cytotoxicity through FMG-mediated fusion, the presence of the HSF1d202–316 transcription factor leads to activation of endogenous HSEs upstream of stress response genes, including hsp70 (Baler, et al., Mol Cell Biol; 13: 2486–2496 (1993); Zuo, et al., supra). Induction of hsp70 is potently immunostimulatory, but optimally so, if it occurs during cell killing in vivo. Expression of HSF-1 is immunotherapeutic, through activation of endogenous HSE elements. Transfection of HSF-1d202–316 induces expression of hsp70 mRNA (see FIG. 12) and induction can be detected at the level of protein expression in a variety of human and murine cell lines (data not shown). HSF-1d202–316 additionally activates expression of other stress-related proteins which also enhance the immunogenicity of the dying tumor cells, such as MICB, a ligand for the NK activatory receptor NKG2D.(data not shown).

Example 12

The Complete HSE-Tyr300-FMG-BSF-1 Feedback Loop can be Incorporated within the Context of a Hybrid LTR Retroviral Vector In one embodiment, the HSE-Tyr300 element was cloned into the 3'LTR of the Mo-MLV derived retroviral vector pBabe Puro (Morgenstern, et al., supra). The HSE-Tyr300 enhancer/promoter was placed in the IJ3 region of the viral LTR as described in Diaz, et al., supra, replacing the viral enhancer and promoter regions of the U3 region of the LTR with the heterologous enhancer/promoter elements (HSE-Tyr-300). Simultaneously, the GALV-FMG cDNA was cloned into the polylinker of the vector. As an added strategy to decrease the chances of initiating the feedback loop in non-melanoma cells, the HSF-1d202–316 cDNA was cloned downstream of the GALV cDNA, separated from it by a linker of 24 base pair (FIG. 14A), thereby exploiting a strategy as described by Cosset, et al., supra.

The lack of an internal ribosome entry site (IRES) between the first (GALV) and the second (HSF-1d202–316) gene in this construct means that only a small proportion of the total mRNA molecules produced from the HSE-Tyr-300 promoter will undergo internal initiation of translation of the second transgene (Cosset, et al., supra). Hence, only those cells in which the promoter is sufficiently active will be able to generate enough mRNA such that any of the second gene is ever translated. Therefore, any non-melanoma cell, in which there is appreciable leakiness of the Tyr-300 element, should still have very low levels of expression of the feedback gene (HSF-1d2g2–3 16), significantly reducing the chances of the feedback loop ever being initiated.

Figure 14A:
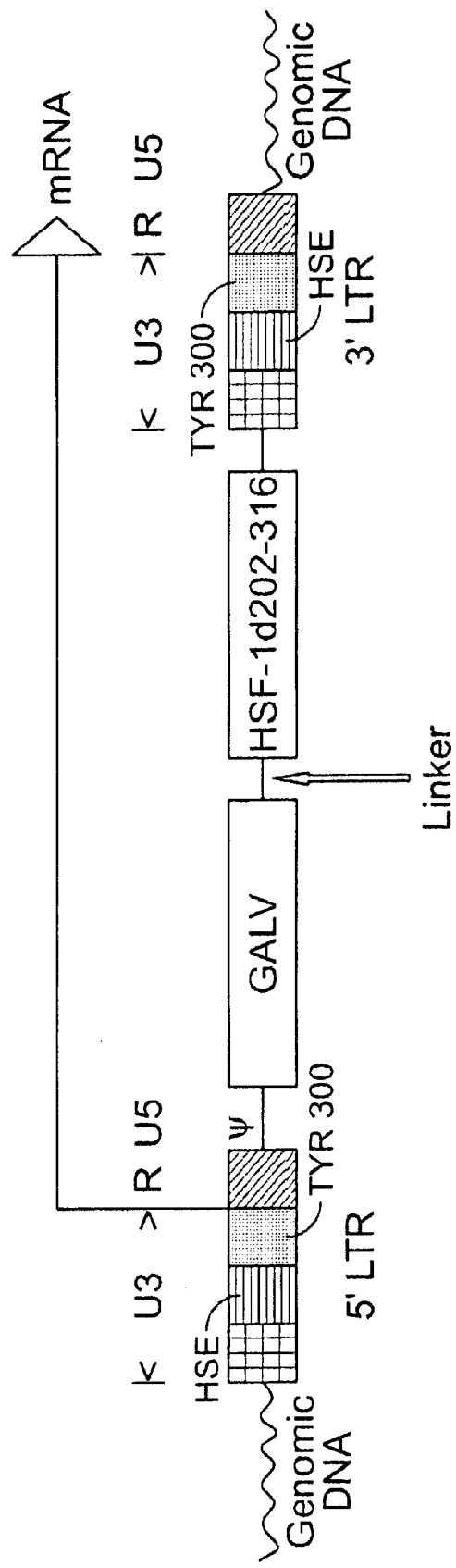
Figure 14C:
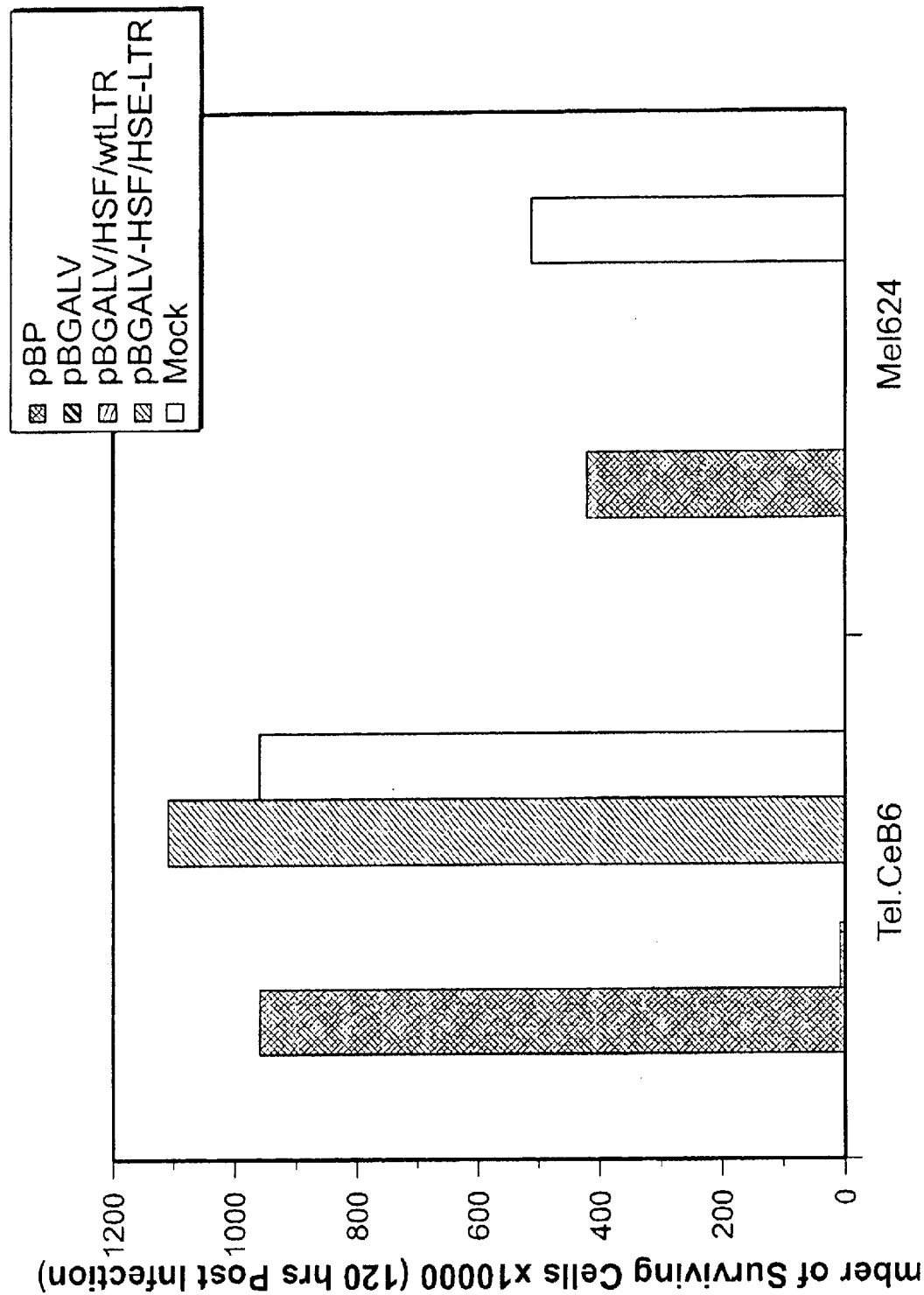

Following packaging, reverse transcription, and integration of the retroviral vector, an integrated provirus of structure shown in FIG. 14A was produced. Virus was packaged from the 2931NT cell line with the VSV-G envelope and used to infect MeWo or MeI624 melanoma and HT1080, 293 or Tel non-melanoma cell lines. The ability of different packaged viral vectors to induce syncytia and cytotoxicity was followed with time (FIGS. 14B, 14C). Whereas the control vector pBabe-Puro generated no detectable syncytia in either melanoma or non-melanoma cell lines, the, positive control vectors pBabe-GALV and pBabe GALV-HSF-1 (wt LTR), in which the GALV cDNA is driven by the Mo-MLV LTR, both induced syncytial formation within 24 hours of infection of all cell types. This led to extensive cell killing over time.

In contrast, the pBabe-GALV-HSF-1 (HSE-Tyr LTR) vector produced no detectable syncytia in either of the three non-melanoma cell lines, indicating that the LTR was unable to drive expression of the GALV cDNA. Further no vector-induced syncytia were observed in infected 293 cells. These cells express the adenoviral E1A gene, which transactivate expression of cellular hsp70 through the HSE element. Despite constitutive transactivation of the HSE element, the tissue specificity of the TYR-300 element was tight enough to prevent initiation of the feedback loop in these cells. However, in the two melanoma cell lines tested, syncytia were induced, but only 48–72 hours following the appearance of syncytia with the wild type LTR. Presumably this is due to the time lag required for the build up to sufficient levels of HSF-1 d202–316 protein to transactivate the HSE element. Thereafter, syncytial development was very aggressive and the pBabe-GALV-HSF-1 (HSE-Tyr LTR) was able to kill over 90% of target melanoma cells, comparable to that of the wild type LTR-driven GALV vector. Finally, to confirm that longer periods of culture did not allow pBabe-GALV-HSF-1 (HSE-Tyr LTR) to induce syncytia, infected TelCeB6 cells were passaged for another week and inspected daily for syncytia. None were detected. Therefore, although there is a clear time delay in the ability of the pBabe-GALV-HSF-1 (HSE-Tyr LTR) vector to become effective, the vector is both highly tissue-specific and effective.

Variations, modifications, and other implementations of what is described herein will occur to those of ordinary skill in the art without departing from the spirit and scope of the invention as claimed. Accordingly, the invention is to be defined not by the preceding illustrative description but instead by the spirit and scope of the following claims.

---

What is claimed is:

1. A composition comprising a nucleic acid, wherein said nucleic acid comprises:
   (a) a cell type-specific promoter for activating the expression of a gene in a specific cell type, wherein the cell type-specific promoter is human Tyr300 (SEQ ID. NO. 1);
   (b) a therapeutic gene sequence operably linked to said cell type-specific promoter;
   (c) an amplification promoter element for amplifying transcription of said therapeutic gene in said specific cell type, wherein said amplification promoter element is a heat shock element (HSE); and
   (d) a sequence encoding a transcription activator, said transcription activator for activating said amplification promoter element, and wherein said transcription activator is heat shock factor-1 (HSF-1).

2. The composition of claim 1, wherein said sequence encoding said transcription activator sequence and said therapeutic gene sequence are on different nucleic acid molecules.

3. The composition of claim 1, wherein said amplification promoter element comprises at least one human HSE consensus sequence.

4. The composition of claim 1, wherein said therapeutic gene is a cytotoxic gene.

5. The composition of claim 4, wherein said cytotoxic gene encodes a fusogenic protein.

6. The composition of claim 4, wherein the cytotoxic gene encodes GALVenv, HSVTK, cytosine deaminase, nitroreductase, or VSV-G glycoprotein.

7. The composition of claim 1, wherein said nucleic acid produces a level of mRNA expression which is at least 100-fold higher in in vitro cells of the specific cell type compared to in vitro cells which are not of the specific cell type.

8. The composition of claim 1, wherein said nucleic acid produces a level of therapeutic gene mRNA expression which is at least 500-fold higher in in vitro cells of the specific cell type compared to in vitro cells which are not of the specific cell type.

9. The composition of claim 1, wherein said nucleic acid produces a level of therapeutic gene mRNA expression which is at least 1000-fold higher in in vitro cells of the specific cell type compared to in vitro cells which are not of the specific cell type.

10. The composition of claim 1, wherein said transcription activator is constitutively expressed.

11. The composition of claim 9, wherein said therapeutic gene sequence and the sequence encoding said transcription activator are both operably linked to said cell type-specific promoter.

12. The composition of claim 1, wherein said therapeutic gene sequence and the sequence encoding said transcription activator are both operably linked to said amplification promoter element.

13. The composition of claim 1, wherein said transcription activator is HSF-1 comprising a deletion of which lacks amino acid residues 202–316.

* * * * *

UNITED STATES PATENT AND TRADEMARK OFFICE
CERTIFICATE OF CORRECTION

PATENT NO. : 6,867,036 B1
DATED : March 15, 2005
INVENTOR(S) : Vile et al.

It is certified that error appears in the above-identified patent and that said Letters Patent is hereby corrected as shown below:

Title page,
Item [56], References Cited, OTHER PUBLICATIONS,
"Carrol and Taichman" reference, delete "Carrol" and insert -- Carroll --;
Insert:
-- Okamoto et al., "Full-Length Sequence of a Hepatitis C Virus Genome Having Poor Homology to Reported Isolates: Comparative Study of Four Distinct Genotypes," Virology, 1992, 188:331-341 --;
"Osterling" reference, delete "Osterling" and insert -- Oestering --;

Column 31,
Line 2, delete "sequence";

Column 32,
Line 10, delete "9" and insert -- 1 --;
Line 19, delete "comprising a deletion of".

Signed and Sealed this

Twenty-first Day of March, 2006

JON W. DUDAS
*Director of the United States Patent and Trademark Office*